(12) United States Patent
Zhao et al.

(10) Patent No.: US 11,747,349 B2
(45) Date of Patent: Sep. 5, 2023

(54) METHOD FOR SIMULTANEOUSLY DETECTING VITAMIN K1 AND VITAMIN K2 IN TRACES OF BLOOD

(71) Applicant: Beijing Harmony Health Medical Diagnostics Co., Ltd., Beijing (CN)

(72) Inventors: Jinbao Zhao, Beijing (CN); Yongjuan Jia, Beijing (CN); Junjun Ni, Beijing (CN)

(73) Assignee: Beijing Harmony Health Medical Diagnostics Co., Ltd., Beijing (CN)

( * ) Notice: Subject to any disclaimer, the term of this patent is extended or adjusted under 35 U.S.C. 154(b) by 249 days.

(21) Appl. No.: 17/257,088

(22) PCT Filed: Sep. 29, 2020

(86) PCT No.: PCT/CN2020/118947
§ 371 (c)(1),
(2) Date: Dec. 30, 2020

(87) PCT Pub. No.: WO2022/067533
PCT Pub. Date: Apr. 7, 2022

(65) Prior Publication Data
US 2022/0326261 A1 Oct. 13, 2022

(51) Int. Cl.
*G01N 33/82* (2006.01)
*G01N 1/34* (2006.01)
(Continued)

(52) U.S. Cl.
CPC .......... *G01N 33/82* (2013.01); *G01N 1/34* (2013.01); *G01N 30/6034* (2013.01);
(Continued)

(58) Field of Classification Search
None
See application file for complete search history.

(56) References Cited

U.S. PATENT DOCUMENTS

2014/0158881 A1    6/2014  Cooper

FOREIGN PATENT DOCUMENTS

CN    204630989 U     9/2015
CN    105158394 A    12/2015
(Continued)

OTHER PUBLICATIONS

Qiao, X. et al. Separation and characterization of phenolic compounds andtriterpenoid saponins in licorice (*Glycyrrhiza uralensis*) using mobilephase-dependent reversed-phase × reversed-phase comprehensive two-dimensional liquid chromatography coupled with mass spectrometry, Journal of Chromatography A (Year: 2015).*

(Continued)

*Primary Examiner* — Xiaoyun R Xu
(74) *Attorney, Agent, or Firm* — BARNES & THORNBURG LLP; Jeffrey R. Stone

(57) ABSTRACT

Provided is a method for simultaneously detecting Vitamin K1 and Vitamin K2 in traces of blood. The method includes: constructing a two-dimensional liquid chromatography-tandem mass spectrometer, establishing an analytical method, and detecting at least three mixed standard solutions using the constructed two-dimensional liquid chromatography-tandem mass spectrometer to obtain a first detection result; fitting standard curve equations respectively corresponding to Vitamin K1 and Vitamin K2; and mixing and centrifuging a blood sample to which an extraction reagent and a certain amount of internal standard substance are added, collecting a supernatant, blowing the supernatant to dry with nitrogen, redissolving the residue, and detecting the dry supernatant using the constructed two-dimensional liquid chromatography-tandem mass spectrometer to obtain a second detection result. In this manner, concentrations of Vitamin K1 and Vitamin K2 in the blood sample are obtained.

13 Claims, 11 Drawing Sheets

(51) Int. Cl.
  *G01N 30/60* (2006.01)
  *G01N 30/72* (2006.01)
  *G01N 30/88* (2006.01)
  *G01N 30/02* (2006.01)

(52) U.S. Cl.
  CPC ......... *G01N 30/7233* (2013.01); *G01N 30/88* (2013.01); *G01N 2030/027* (2013.01); *G01N 2030/8822* (2013.01)

(56) References Cited

FOREIGN PATENT DOCUMENTS

| CN | 107290447 A | 10/2017 |
|---|---|---|
| CN | 109828058 A | 5/2019 |
| CN | 110208437 A | 9/2019 |
| CN | 110208438 A | 9/2019 |
| CN | 110824057 A | 2/2020 |
| CN | 110927310 A | 3/2020 |
| JP | 2004504141 A | 2/2004 |

OTHER PUBLICATIONS

Written Opinion of the International Searching (China National Intellectual Property Administration), PCT/CN2020/118947, filed Sep. 29, 2020. (English translation attached).

Supplementary European Search Report issued in European Patent Application No. EP 20 82 7981, dated Jun. 3, 2022.

P.M.M. Van Haard et al., "Quantitation of trans-vitamin K1 in small serum samples by off-line multidimensional liquid chromatography", Clinica Chimica Acta, 157 (1986) 221-230.

IDA Boegh Andersen et al., "Quantitation of vitamin K1 in serum using online SPE-LC-MS/MS and the challenges of working with vitamin K", Journal of Chromatography B 1117 (2019) 41-48.

International Search Report issued in PCT application No. PCT/CN2020/118947, dated Jun. 24, 2021.

* cited by examiner

METHOD FOR SIMULTANEOUSLY DETECTING VITAMIN K1 AND VITAMIN K2 IN TRACES OF BLOOD

TECHNICAL FIELD

The present application relates to the technical field of biological detection, for example, relates to a method for simultaneously detecting Vitamin K1 and Vitamin K2 in traces of blood.

BACKGROUND

Vitamin K1 (i.e., Phylloquinone) is widely found in natural green plants. Such a vitamin is stable to air and moisture, but is decomposed when exposed to sunlight. In addition, Vitamin K1 plays an important role in maintaining normal blood coagulation in the body and plays an auxiliary role in activating some blood coagulation factors and anticoagulant proteins.

Vitamin K2 (i.e., Menaquinone-4), acting as a bone density protector and a metabolite in humans, has potential antitumor activity, and has been used in studies of the treatment of diabetes, osteoporosis, pre-diabetic states, and liver cancer.

High performance liquid chromatography (HPLC) and liquid chromatography-tandem mass spectrometry (LC-MS/MS) are the main methods for the detection of Vitamin K1 and Vitamin K2 in blood currently reported in the literature. Most of the existing methods reported in the literature have various problems such as detection item singleness, slow detection speed, long analysis time, a large amount of collected blood, and high cost. Among these problems, the single detection of Vitamin K1 is the most common. Due to the low content of Vitamin K2 in the human body, in the report of existing literature, the amount of blood used for pre-treatment would be increased to meet the sensitivity requirements of the detection, but such a method is not suitable for large quantities of clinical detections.

SUMMARY

The object of the present application is to provide a two-dimensional liquid chromatography-tandem mass spectrometry analysis method for simultaneously detecting Vitamin K1 and vitamin K2 in traces of blood, which is simple in operation, fast in analysis and suitable in a wide range.

The embodiments of the present application provide a method for simultaneously detecting Vitamin K1 and Vitamin K2 in blood, including:

(1) establishment of an analytical method for detecting Vitamin K1 and Vitamin K2 in blood, including the selection of two-dimensional liquid chromatography-tandem mass spectrometer system modules, the construction of a two-dimensional liquid chromatography-tandem mass spectrometer system, and the establishment of analytical conditions of the two-dimensional liquid chromatography-tandem mass spectrometer;

(2) standardization of standard solutions (2a) preparing at least three mixed standard solutions, where the mixed standard solution is a solution having an internal standard substance, Vitamin K1, and Vitamin K2, and the concentration of the internal standard substance in the at least three mixed standard solutions is the same;

(2b) detecting each of the at least three mixed standard solutions with the two-dimensional liquid chromatography-tandem mass spectrometer using the analytical method established in Step (1) to obtain first detection results respectively corresponding to the at least three mixed standard solutions;

(2c) fitting standard curve equations respectively corresponding to Vitamin K1 and Vitamin K2 according to each of the first detection results and concentrations of the internal standard substance, Vitamin K1 and Vitamin K2 in the mixed standard solutions; and (3) detection of a blood sample (3a) adding the same amount of internal standard substance as in the mixed standard solution to the blood sample, adding an extraction reagent, performing centrifugation after the extraction, collecting a supernatant obtained after the centrifugation, blowing the supernatant to dry, and redissolving the residue with a redissolution solution to obtain an analytical sample;

(3b) detecting the blood sample with the two-dimensional liquid chromatography-tandem mass spectrometer using the analytical method established in Step (1) to obtain a second detection result corresponding to the blood sample;

(3c) obtaining concentrations of Vitamin K1 and Vitamin K2 in the blood sample based on the second detection result and the standard curve equations respectively corresponding to Vitamin K1 and Vitamin K2.

The above analytical method involved in the present application can simultaneously detect Vitamin K1 and Vitamin K2 in blood, and effectively shorten the detection time to 5.5 min, thereby reducing the detection cost. Through the constructed two-dimensional liquid chromatography-tandem mass spectrometer, the analytical method gains high sensitivity and strong specificity, and thus is suitable for the simultaneous detection of Vitamin K1 and Vitamin K2 in blood samples, especially for the detection of traces of blood sample (20-200 µL), including fingertip blood or heel blood, so that the patient's pain caused by blood collection can be reduced. The pre-treatment operation of this analytical method is simple, and thus this analytical method can be easily automated, thereby greatly reducing the detection interference and improving the detection sensitivity. Through this analytical method, the analysis is fast and the detection time is short, thereby reducing the detection cost.

As an optional technical solution, the two-dimensional liquid chromatography-tandem mass spectrometer system modules in Step (1) include a liquid chromatography pump, an auto sampler, a column oven, and a mass spectrum analyzer;

wherein the number of sets of liquid chromatography pumps is at least two, wherein one of the at least two sets of liquid chromatography pumps is connected to the auto sampler, and the resting of the at least two sets of liquid chromatography pumps complete a liquid-pumping process independently;

the auto sampler is used for completing a sample injection process;

the column oven includes at least one set of switching valves and is used for completing a two-dimensional liquid chromatography column switching process; and each of the at least one set of switching valves is independently selected from a six-way switching valve or a ten-way switching valve.

As an optional technical solution, the construction of the two-dimensional liquid chromatography-tandem mass spectrometer system in Step (1) includes:

connecting one set of liquid chromatography pumps in series to the auto sampler, and connecting the auto sampler to a first dimensional chromatographic column, and connecting the first dimensional chromatographic column to the switching valve; connecting another set of liquid chromatography pumps to the switching valve, connecting the switching valve to a second dimensional chromatographic column, and connecting the second dimensional chromatographic column to the mass spectrum analyzer; and controlling an analysis state of the system through the switching valve, where the analysis state includes three states, i.e., sample injection, two-dimensional transfer, and analysis;

when the analysis state of the system is the sample injection state, a sample is analyzed by the first dimensional chromatographic column, and non-target analytes are discharged as a waste liquid from the switching valve;

when the analysis state of the system is the two-dimensional transfer state, the first dimensional chromatographic column is connected in series to the second dimensional chromatographic column, and a target analyte is transferred from the first dimensional chromatographic column to the second dimensional chromatographic column;

when the analysis state of the system is the analysis state, the sample is analyzed by the second dimensional chromatographic column, and the mass spectrum analyzer is connected to perform data collection.

As an optional technical solution, the establishment of analytical conditions of the two-dimensional liquid chromatography-tandem mass spectrometer in Step (1) includes:

setting the flow rate of the mobile phase of two-dimensional liquid chromatography to 0.5-2.0 mL/min;

wherein the mobile phase is a polar solvent including ultrapure water, methanol, acetonitrile, and any mixture of any two or three thereof in any proportion, and the mobile phase includes 0.01% to 1% formic acid;

setting the sample injection amount of two-dimensional liquid chromatography to 1-100 µL;

setting the column temperature of the column oven of two-dimensional liquid chromatography to 20-60° C.; and configuring the mass spectrum analyzer to adopt an atmospheric pressure chemical ionization (APCI) source and a positive ion scan mode; and setting the flow rate of atomized gas to 0.5-3 L/min, the flow rate of heated gas to 3-20 L/min, the temperature of the ion source to 100-400° C., the temperature of the desolvent tube to 30-300° C., the temperature of the heating block is 30-500° C., the flow rate of dry gas to 0-20 L/min, and the interface voltage to 1-5 kV.

As an optional technical solution, the establishment of analytical conditions of the two-dimensional liquid chromatography-tandem mass spectrometer in Step (1) includes:

selecting a phenylhexyl column as the first dimensional chromatographic column of two-dimensional liquid chromatography; and a C18 column as the second dimensional chromatographic column.

The best separation of endogenous impurities in the blood can be implemented by specifically selecting a phenylhexyl column as the first dimensional chromatographic column and a C18 column as the second dimensional chromatographic column.

As an optional technical solution, the internal standard substance includes a Vitamin K1 isotope marker and a Vitamin K2 isotope marker.

As an optional technical solution, two variables of the standard curve equation corresponding to Vitamin K1 are: a ratio of a chromatographic peak area of Vitamin K1 to a chromatographic peak area of an internal standard substance corresponding to Vitamin K1, and a ratio of a concentration of Vitamin K1 to a concentration of the internal standard substance corresponding to Vitamin K1, respectively; and two variables of the standard curve equation corresponding to Vitamin K2 are: a ratio of a chromatographic peak area of Vitamin K2 to a chromatographic peak area of an internal standard substance corresponding to Vitamin K2, and a ratio of a concentration of Vitamin K2 to a concentration of the internal standard substance corresponding to Vitamin K2, respectively.

As an optional technical solution, the method for preparing the at least three mixed standard solutions in Step (2a) includes:

preparation of standard mixed intermediate solutions: mixing a Vitamin K1 standard stock solution and a Vitamin K2 standard stock solution in different proportions, diluting the obtained mixed solutions with a diluent to obtain the standard mixed intermediate solutions of at least three different concentrations, and storing the standard mixed intermediate solutions from light; preparation of a mixed internal standard working solution: mixing a Vitamin K1 internal standard substance stock solution and a Vitamin K2 internal standard substance stock solution in different proportions, diluting the obtained mixed solution with a diluent to obtain the mixed internal standard working solution, and storing the mixed internal standard working solution from light; and preparation of the mixed standard solutions: pipetting the same volume of at least three standard mixed intermediate solutions that have different concentrations respectively, adding the same volume of the mixed internal standard working solution and the same volume of the diluent to each of the at least three standard mixed intermediate solutions, and mixing the obtained mixtures with vortexes at 1500-3000 r/min for 30 s to 1 min to prepare the at least three different mixed standard solutions;

wherein the diluent includes methanol or an aqueous methanol solution, acetonitrile or an aqueous acetonitrile solution, and isopropanol or an aqueous isopropanol solution, and volume concentrations of the aqueous methanol solution, the acetonitrile aqueous solution and the isopropanol aqueous solution are independently selected from 50% to 100%.

As an optional technical solution, in the standard mixed intermediate solution, Vitamin K1 has a concentration of 0.05-500 ng/mL, and Vitamin K2 has a concentration of 0.05-500 ng/mL; and in the mixed internal standard working solution, the Vitamin K1 internal standard substance has a concentration of 10-30 ng/mL, and the Vitamin K2 internal standard substance has a concentration of 10-30 ng/mL.

As an optional technical solution, the blood sample includes whole blood, serum, or plasma.

The analytical method involved in the present application is suitable for blood samples of whole blood, serum, or plasma, and has a wide range of application.

As an optional technical solution, the blood sample is used in an amount of 20 µL or more.

The analytical method involved in the present application only needs the very traces of blood sample such as fingertip blood or heel blood to complete the detection so that the patient's pain caused by blood collection can be reduced.

As an optional technical solution, before Step (3a), the method further includes:

centrifuging the blood sample at a centrifugation speed of 1000-3000 r/min for 10-20 min, using a supernatant obtained after the centrifugation as the blood sample, and storing the blood sample at −80° C.

As an optional technical solution, Step (3a) includes:

adding the same amount of internal standard substance as in the mixed standard solution to the blood sample, adding an extraction reagent, mixing the blood sample with vortexes and oscillation for 5-15 min at a rotating speed of 1000-2500 r/min after the extraction, centrifuging the blood sample for 5-15 min at a rotating speed of 10000-15000 r/min, collecting some or all of a supernatant obtained after the centrifugation, blowing the same to dry with nitrogen under a nitrogen blower, redissolving the residue with a redissolution solution, and mixing the obtained mixture with vortexes and oscillation at a rotating speed of 1000-2500 r/min for 1-5 min to obtain an analytical sample.

As an optional technical solution, the extraction reagent is a combination of a polar extraction reagent and a non-polar extraction reagent;

the polar extraction reagent includes any one or a combination of at least two of methanol, ethanol, acetonitrile, acetone, or isopropanol;

the non-polar extraction reagent includes any one or a combination of at least two of n-hexane, cyclohexane, n-octane, or petroleum ether; and wherein the redissolution solution includes any one or a combination of at least two of methanol, ethanol, or acetonitrile.

In the embodiments of the present application, at least three mixed standard solutions of different concentrations each are detected using the two-dimensional liquid chromatography-tandem mass spectrometer, where the mixed standard solution is a solution of Vitamin K1 and Vitamin K2, such a solution further has an internal standard substance, and the concentration of the internal standard substance in the at least three mixed standard solutions is the same; the fitting is performed according to detection results of the at least three mixed standard solutions of different concentrations to obtain the standard curve equations respectively corresponding to Vitamin K1 and Vitamin K2; the same amount of internal standard substance working solution as in the mixed standard solution is added to a blood sample, then an extraction reagent is added and mixed well with the blood sample to perform extraction, the blood sample is then centrifuged at a high speed, a supernatant obtained after the centrifugation is collected, the supernatant is blown to dry with nitrogen, the supernatant is redissolved using a redissolution solution, and the obtained mixture is mixed well to obtain the supernatant with interference substances removed. The obtained supernatant is detected using the constructed two-dimensional liquid chromatography-tandem mass spectrometer, and concentrations of Vitamin K1 and Vitamin K2 in the blood sample are obtained based on the detection results and the standard curve equations of Vitamin K1 and Vitamin K2. The significantly beneficial effects of this method are as follows: this method can simultaneously detect Vitamin K1 and Vitamin K2 in blood, and effectively shorten the detection time to 5.5 min, thereby reducing the detection cost. Through the constructed two-dimensional liquid chromatography-tandem mass spectrometer, the analytical method gains high sensitivity and strong specificity, greatly reduces the detection interference and thus is suitable for the simultaneous detection of Vitamin K1 and Vitamin K2 in blood samples, especially for the detection of traces of blood sample (20-200 µL), including fingertip blood or heel blood, so that the patient's pain caused by blood collection can be reduced. The pre-treatment operation of this analytical method is simple, and thus this analytical method can be easily automated. Through this analytical method, the analysis is fast and the detection time is short, thereby reducing the detection cost.

BRIEF DESCRIPTION OF DRAWINGS

To illustrate the technical solutions in the embodiments of the present disclosure or the technical solutions in the existing art more clearly, drawings used in the description of the embodiments or the existing art will be briefly described below. Apparently, the drawings described below illustrate part of the embodiments of the present disclosure, and those of ordinary skill in the art may obtain other drawings based on the drawings described below on the premise of paying no creative work.

DETAILED DESCRIPTION

Figure 1:
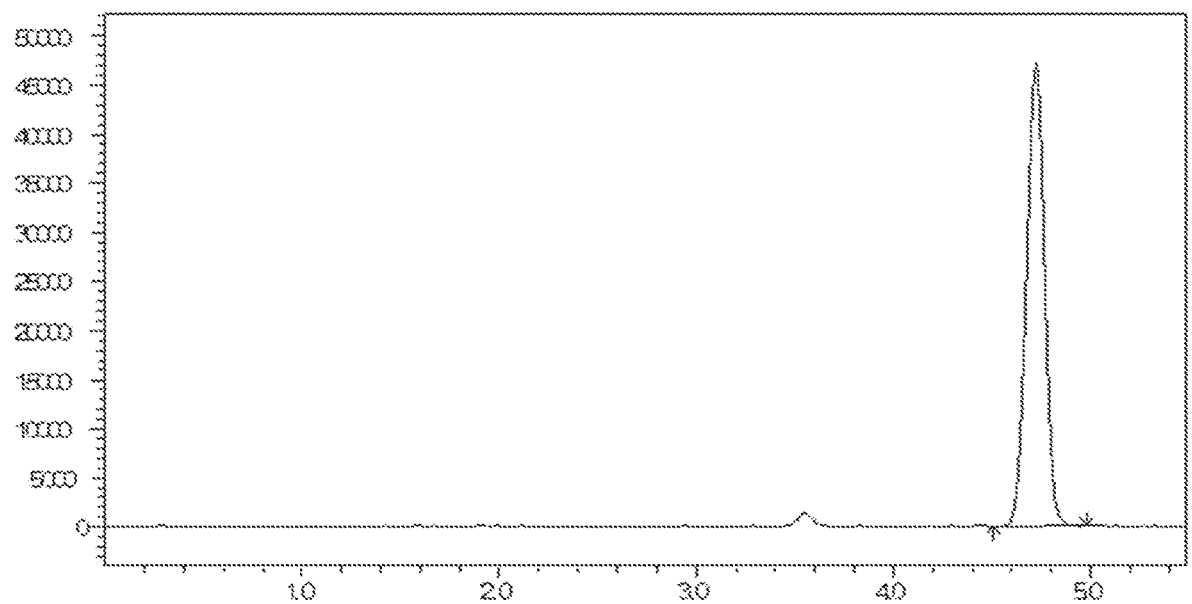
FIG. 1 is a chromatogram of Vitamin K1 in a mixed standard solution provided by an example of the present disclosure.

To illustrate the object, technical solutions and advantages of the present disclosure more clearly, the technical solutions of the present disclosure will be described clearly and completely in conjunction with drawings. Apparently, the examples described below are part, not all, of examples of the present disclosure. Based on the examples of the present disclosure, all other examples obtained by those of ordinary skill in the art without creative work are within the scope of the present disclosure.

The examples of the present disclosure provide a two-dimensional liquid chromatography-tandem mass spectrometry analytical method for simultaneously detecting Vitamin K1 and Vitamin K2 in traces of blood. The analytical method includes steps described below.

In step 101, a two-dimensional liquid chromatography-tandem mass spectrometer is constructed, a two-dimensional liquid chromatography-tandem mass spectrometry analytical method for detecting Vitamin K1 and Vitamin K2 in traces of blood is established, and detection conditions are preset.

In step 102, mixed standard solutions of at least three concentrations are prepared, where the mixed standard solution is a solution having an internal standard substance, Vitamin K1, and Vitamin K2, and the concentration of the internal standard substance in the mixed standard solutions of at least three concentrations is the same.

In step 103, each of the mixed standard solutions is detected under the preset detection conditions using the two-dimensional liquid chromatography-tandem mass spectrometry analytical method to obtain first detection results respectively corresponding to the mixed standard solutions of at least three concentrations.

In step 104, standard curve equations respectively corresponding to Vitamin K1 and Vitamin K2 are fitted according to each of the first detection results and concentrations of Vitamin K1, Vitamin K2 and the internal standard substance in the mixed standard solutions.

In step 105, an extraction reagent and an internal standard substance having the same concentration as in the mixed standard solutions are added to a blood sample, then mixed well, extracted, and centrifuged at a high speed, and a supernatant obtained after the centrifugation is collected, blown to dry with nitrogen, redissolved with a redissolution solution, and mixed well to obtain an analytical sample.

In step 106, the analytical sample is detected under the detection conditions using the two-dimensional liquid chromatography-tandem mass spectrometry analytical method to obtain a second detection result corresponding to the blood sample.

In step 107, concentrations of Vitamin K1 and Vitamin K2 in the blood sample are obtained based on the second detection result and the standard curve equations respectively corresponding to Vitamin K1 and Vitamin K2.

The detection process with the two-dimensional liquid chromatography-tandem mass spectrometer used in the detection method provided by this example of the present disclosure may be as follows: constructing a standard curve equation of the chromatographic peak area of a standard target substance versus the concentration of the standard target substance based on the relationship between the chromatographic peak area of the standard target substance and the concentration of the standard target substance in the mixed standard solutions, substituting the chromatographic peak area of a target substance in a blood sample into the standard curve equation, and then calculating to obtain the concentration of the target substance in the blood sample.

It is to be understood that the preceding first detection results refer to chromatographic peak areas of Vitamin K1 and Vitamin K2 in the spectrum of the mixed standard solution of each concentration.

However, due to the blood sample treatment process and detection errors, there is a certain deviation in the preceding standard curve equation constructed based on the chromatographic peak area of the standard target and the concentration of the standard target, and thus there are also deviations in the concentration of the target in the blood sample calculated based on the standard curve equation. More preferably, the detection process with the two-dimensional liquid chromatography-tandem mass spectrometer used in the detection method may also be as follows: using a ratio of the chromatographic peak area of the target substance to the chromatographic peak area of the internal standard substance as a first independent variable, using a ratio of the concentration of the target substance to the concentration of the internal standard substance as a second independent variable, performing linear regression fitting according to at least three groups of first independent variables and second independent variables to obtain a standard curve equation, substituting a ratio of the chromatographic peak area of the target substance to the chromatographic peak area of the internal standard substance in the blood sample into the standard curve equation to obtain the chromatographic peak area of the target substance and the concentration of the internal standard substance in the blood sample, and calculating a ratio of the concentration of the target substance to the concentration of the internal standard substance in the blood sample, and thus calculating the concentration of the target substance in the blood sample since the concentration of the internal standard substance is known.

Optionally, both the target substance in the blood sample and the standard target substance are Vitamin K1 and Vitamin K2.

Optionally, the internal standard substance is a Vitamin K1 isotope marker (D7-Vitamin K1) and a Vitamin K2 isotope marker (D7-Vitamin K2).

The Vitamin K1 isotope marker (D7-Vitamin K1) corresponds to Vitamin K1, and the Vitamin K2 isotope marker (D7-Vitamin K2) corresponds to Vitamin K2.

Optionally, two variables of the standard curve equation corresponding to Vitamin K1 are: a ratio of a chromatographic peak area of Vitamin K1 to a chromatographic peak area of the Vitamin K1 isotope marker (D7-Vitamin K1), and a ratio of a concentration of Vitamin K1 to a concentration of the Vitamin K1 isotope marker (D7-Vitamin K1), respectively; and two variables of the standard curve equation corresponding to Vitamin K2 are: a ratio of a chromatographic peak area of Vitamin K2 to a chromatographic peak area of the Vitamin K2 isotope marker (D7-Vitamin K2), and a ratio of a concentration of Vitamin K2 to a concentration of the Vitamin K2 isotope marker (D7-Vitamin K2), respectively.

It is known in the above description that the way in which the blood sample is treated also affects the final detection result. In examples of the present disclosure, the same amounts of internal standard substance and extraction reagent as in the mixed standard solution are added to the blood sample, the above materials are mixed well, then extracted and centrifuged at a high speed, a supernatant obtained after the centrifugation is collected, blown to dry with nitrogen, redissolved with a redissolution solution, and mixed well to obtain the analytical sample. In this manner, Vitamin K1 and Vitamin K2 in the blood sample can be retained maximally, and at the same time, interference substances can be removed. Since the pre-treatment steps are simple and thus easy to automate, the time for pre-treating the blood sample can be greatly shortened, thereby shortening the detection time and improving the detection efficiency of the blood sample.

Generally speaking, the preparation manner of the mixed standard solution directly affects the accuracy of the detection, and the manner used in this example for preparing the mixed standard solution can ensure the accuracy of the detection result. In an example of the present disclosure, the step of preparing the mixed standard solutions of at least three concentrations includes:

preparation of standard mixed intermediate solutions: mixing a Vitamin K1 standard stock solution and a Vitamin K2 standard stock solution in different proportions, diluting the obtained mixed solutions with a diluent to obtain at least three standard mixed intermediate solutions of different concentrations, and storing the standard mixed intermediate solutions at −80° C. from light;

preparation of a mixed internal standard working solution: mixing a Vitamin K1 internal standard substance stock solution and a Vitamin K2 internal standard substance stock solution in different proportions, diluting the obtained mixed solution with a diluent to obtain the mixed internal standard working solution, and storing the mixed internal standard working solution at −80° C. from light; and preparation of the mixed standard solutions: pipetting the same volume of at least three standard mixed intermediate solutions that have different concentrations respectively, adding the same volume of the mixed internal standard working solution and the same volume of the diluent to the standard mixed intermediate solution of each concentration, and mixing each obtained mixture with vortexes at 1500-3000 r/min for 30 s to 1 min to prepare the at least three mixed standard solutions of different concentrations.

An internal standard substance having the same concentration as in the mixed standard solutions is added to the blood sample, two extraction reagents are then added, the above materials are mixed well, then extracted and centrifuged at a high speed, a supernatant obtained after the centrifugation is obtained, the supernatant is blown to dry, the residue is redissolved with a redissolution solution, and the solution is mixed well to obtain an analytical sample. The blood sample involved in the examples of the present disclosure may be the blood, or may be related samples of the blood such as whole blood, serum, plasma, and the like.

The method of detecting Vitamin K1 and Vitamin K2 in traces of blood is illustrated in detail in the following examples by using serum (20 μL) collected from selected volunteers by our company.

Example 1

Construction of Two-Dimensional Liquid Chromatography-Tandem Mass Spectrometer and Preset Detection Conditions A two-dimensional liquid chromatography-tandem mass spectrometer was constructed, and its system modules included:

two sets of liquid chromatography pumps, where one set of liquid chromatography pumps was connected to the auto sampler, and the other set of liquid chromatography pumps completed a liquid-pumping process independently;

one auto sampler, used for completing a sample injection process;

one column oven, which included two sets of switching valves which were six-way switching valves; and a mass spectrum analyzer, provided with an APCI source.

The two-dimensional liquid chromatography-tandem mass spectrometer was constructed, and its system connections included configurations where:

one set of liquid chromatography pumps was connected in series to the auto sampler, the auto sampler was connected to a first dimensional chromatographic column, and the first dimensional chromatographic column was connected to the switching valve; the other set of liquid chromatography pumps was connected to the switching valve, the switching valve was connected to a second dimensional chromatographic column, and the second dimensional chromatographic column was connected to the mass spectrum analyzer; and the switching valve controlled the analysis state of the system, where the analysis state included three states, i.e., sample injection, two-dimensional transfer, and analysis, and where when the analysis state of the system was the sample injection state, the sample was analyzed by the first dimensional chromatographic column, and non-target analytes were discharged as waste liquid from the switching valve;

when the analysis state of the system was the two-dimensional transfer state, the first dimensional chromatographic column was connected in series to the second dimensional chromatographic column, and the target analyte was transferred from the first dimensional chromatographic column to the second dimensional chromatographic column; and when the analysis state of the system was the analysis state, the sample was analyzed by the second dimensional chromatographic column, and the mass spectrum analyzer was connected to perform data collection.

The two-dimensional liquid chromatography-tandem mass spectrometer was constructed, and the preset detection conditions included the following:

corresponding chromatographic conditions in the preset detection conditions for the two-dimensional high performance liquid chromatography in the two-dimensional liquid chromatography-tandem mass spectrometer for detecting Vitamin K1 and Vitamin K2 in the blood sample, including:

two sets of liquid chromatography pumps, where their mobile phases were methanol (containing 0.2% formic acid), the flow rate was 1.2 mL/min, and isocratic elution was performed for 5.50 min;

a column oven, where the column temperature was 50° C., and the chromatographic columns were Kinetex Phenyl-Hexyl 2.6 μm 100*4.6 mm and Kinetex C18 2.6 μm 100*4.6 mm; and where two six-way switching valves were included, where the left valve location was 1-2 at 0.00 min, the left valve location was 1-6 at 1.40 min, and the left valve location was 1-2 at 1.85 min, while the right valve location was 1-6 all the time; and an auto sampler, where the temperature of the auto sampler was 15° C., the needle wash solution was methanol, and the sample injection amount was 30 μL; and corresponding spectrometry conditions in the preset detection conditions for the spectrometry in the two-dimensional liquid chromatography-tandem mass spectrometer for detecting Vitamin K1 and Vitamin K2 in the blood sample, including conditions where:

an APCI source and a positive ion scan mode were adopted, the flow rate of atomized gas was 1.5 L/min, the temperature of an ion source was 400° C., the temperature of the desolvent tube was 200° C., the temperature of the heating block was 300° C., and the flow rate of dry gas was 0 L/min; and the interface voltage was 5 kV, the collision gas was argon, and the parameter setting was 200 kPa.

Furthermore, parameters of detection ion pairs for the spectrometry in the two-dimensional liquid chromatography-tandem mass spectrometer are shown in Table 1.

TABLE 1

| Material name | Parent ion | Daughter ion | Scan time | Q1 offset voltage | Collusion voltage | Q3 offset voltage |
|---|---|---|---|---|---|---|
| Vitamin K1* | 451.2 | 187 | 60 | −10 | −26 | −19 |
| Vitamin K1 | 451.2 | 105 | 60 | −10 | −50 | −19 |
| D7-Vitamin K1-IS* | 458.2 | 194 | 60 | −10 | −26 | −19 |
| D7-Vitamin K1 | 458.2 | 112 | 60 | −10 | −50 | −19 |
| Vitamin K2* | 445.25 | 187.25 | 60 | −10 | −25 | −19 |
| Vitamin K2 | 445.25 | 259.5 | 60 | −10 | −20 | −19 |
| D7-Vitamin K2* | 452.25 | 194.25 | 60 | −10 | −25 | −19 |
| D7-Vitamin K2 | 452.25 | 259.25 | 60 | −10 | −20 | −19 |

*represents quantitative ion

Example 2

Preparation of Mixed Standard Solutions of a Series of Concentrations

Preparation of standard mixed intermediate solutions: a Vitamin K1 standard stock solution and a Vitamin K2 standard stock solution, which were of the same volume, were pipetted;

the pipetted Vitamin K1 standard stock solution whose concentration was 100 μg/mL and the Vitamin K2 standard stock solution whose concentration was 100 μg/mL were mixed and then diluted with a 90% aqueous methanol solution to obtain 9 standard mixed intermediate solutions of different concentrations, and these standard mixed intermediate solutions were stored at −80° C. from light;

where in these standard mixed intermediate solutions of different concentrations, the concentration of Vitamin K1 in each serially diluted solution was 0.05 ng/mL, 0.1 ng/mL, 0.2 ng/mL, 0.5 ng/mL, 2 ng/mL, 10 ng/mL, 50 ng/mL, 200 ng/mL, and 500 ng/mL, respectively; and the concentration of Vitamin K2 in each serially diluted solution was 0.05 ng/mL, 0.1 ng/mL, 0.2 ng/mL, 0.5 ng/mL, 2 ng/mL, 10 ng/mL, 50 ng/mL, 200 ng/mL, and 500 ng/mL, respectively.

Preparation of a mixed internal standard working solution: a Vitamin K1 internal standard substance stock solution whose concentration was 100 μg/mL and a Vitamin K2 internal standard substance stock solution whose concentration was 100 μg/mL were pipetted, mixed and then diluted with a 90% aqueous methanol solution to 20 ng/mL to obtain the mixed internal standard working solution.

Preparation of mixed standard solutions: 20 μL of each of 9 standard mixed intermediate solutions of different concentrations was pipetted, and 10 μL of the mixed internal standard working solution and 70 μL of methanol were added to each of the pipetted standard mixed intermediate solutions of different concentrations and then mixed with vortexes at 2500 r/min for 1 min to prepare 9 mixed standard solutions of different concentrations.

Example 3

Fitting of Standard Curve Equations

Each of mixed standard solutions of different concentrations obtained in Example 1 was detected using the constructed two-dimensional liquid chromatography-tandem mass spectrometer to obtain spectra of 9 mixed standard solutions of different concentrations.

Chromatographic peak areas of Vitamin K1, Vitamin K2, the Vitamin K1 isotope marker (D7-Vitamin K1) and the Vitamin K2 isotope marker (D7-Vitamin K2) were obtained from the spectrum of each of the mixed standard solutions of different concentrations, respectively.

The ratio of the chromatographic peak area of Vitamin K1 to the chromatographic peak area of the Vitamin K1 isotope marker (D7-Vitamin K1) in the above-mentioned 9 mixed standard solutions of different concentrations was used as the ordinate $y_1$ of the standard curve equation $q_1$, and the ratio of the chromatographic peak area of Vitamin K2 to the chromatographic peak area of the Vitamin K2 isotope marker (D7-Vitamin K2) was used as the ordinate $y_2$ of the standard curve equation $q_2$.

The ratio of the concentration of Vitamin K1 to the concentration of the Vitamin K1 isotope marker (D7-Vitamin K1) in the above-mentioned 9 mixed standard solutions of different concentrations was used as the abscissa $x_1$ of the standard curve equation $q_1$, and the ratio of the concentration of Vitamin K2 to the concentration of the Vitamin K2 isotope marker (D7-Vitamin K2) was used as the abscissa $x_2$ of the standard curve equation $q_2$.

The linear regression fitting was performed on data about the above-mentioned 9 different concentrations, where the weighting coefficient for fitting was $1(x^2)$, to obtain the standard curve equation $q_1$ corresponding to Vitamin K1, i.e., $y_1=a*x_1+b$, and the standard curve equation $q_2$ corresponding to Vitamin K2, i.e., $y_2=c*x_2+d$, where a and c were the slopes of the respective standard curve equations, and b and d were the intercepts of the respective standard curve equations.

It is to be noted that the standard curve equations and the weighting coefficient were required to be re-measured before each detection. That is, Example 3 was the steps that must be performed for detecting Vitamin K1 and Vitamin K2 in the blood within a period of time. This period of time was generally the effective period of time of the mixed standard solutions.

Figure 2:
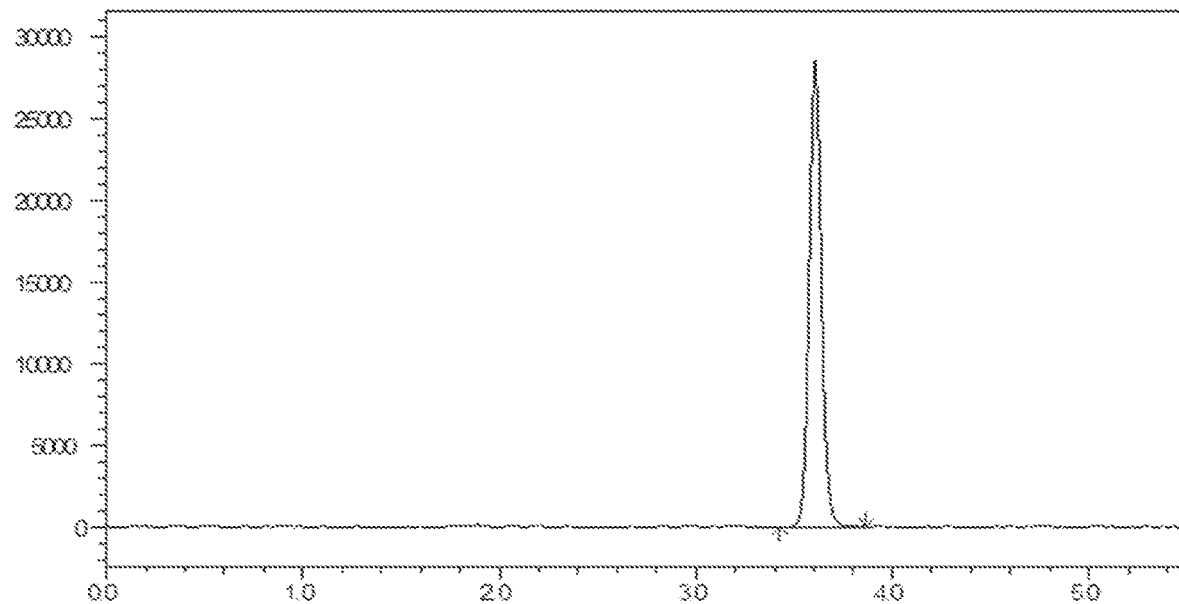
FIG. 2 is a chromatogram of Vitamin K2 in a mixed standard solution provided by an example of the present disclosure.
Figure 3:
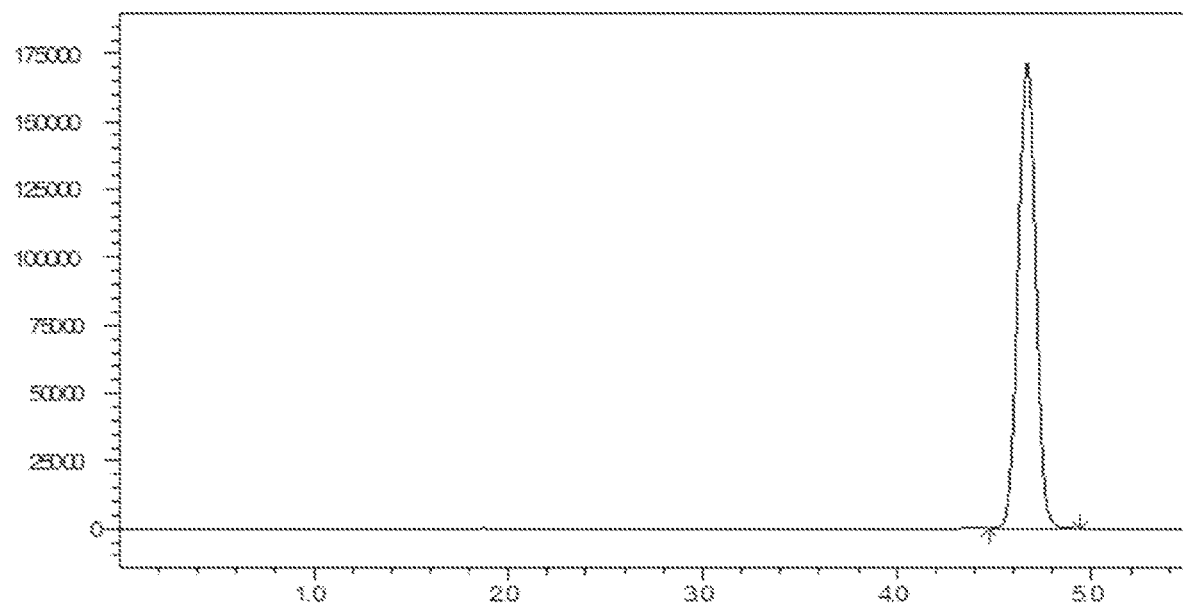
FIG. 3 is a chromatogram of a Vitamin K1 isotope marker (D7-Vitamin K1) in a mixed standard solution provided by an example of the present disclosure.
Figure 4:
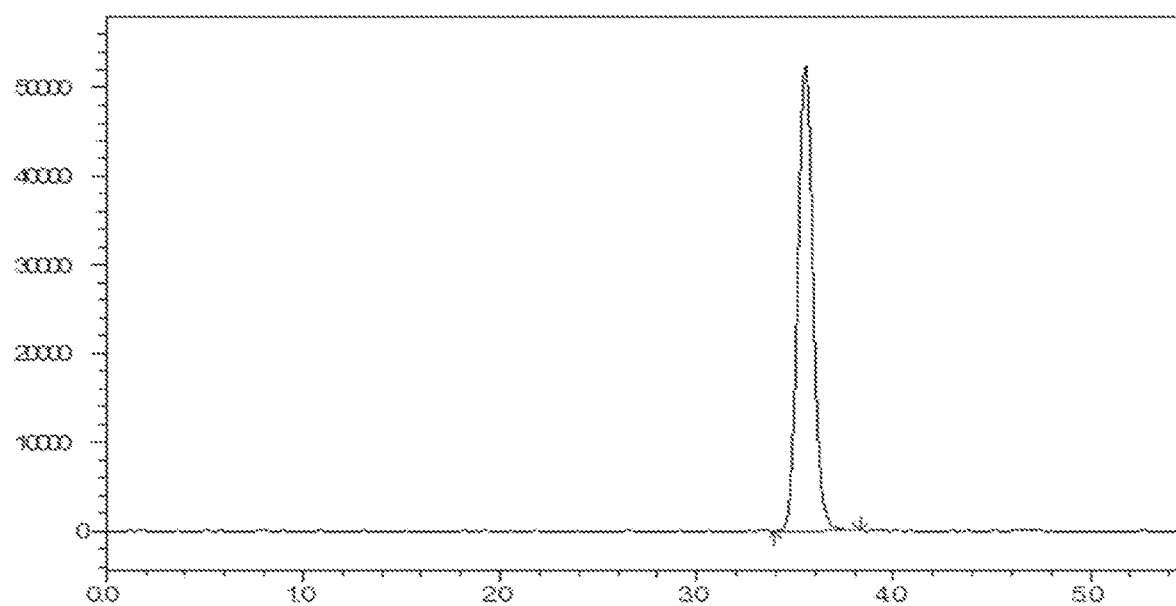
FIG. 4 is a chromatogram of a Vitamin K2 isotope marker (D7-Vitamin K2) in a mixed standard solution provided by an example of the present disclosure.

The chromatogram of Vitamin K1 in a mixed standard solution of the above example was shown in FIG. 1, the chromatogram of Vitamin K2 in a mixed standard solution was shown in FIG. 2, the chromatogram of the Vitamin K1 isotope marker (D7-Vitamin K1) in a mixed standard solution was shown in FIG. 3, and the chromatogram of the Vitamin K2 isotope marker (D7-Vitamin K2) in a mixed standard solution was shown in FIG. 4.

In the mixed standard solution, the retention time of Vitamin K1 was 4.700 min, and the retention time of Vitamin K2 was 3.600 min.

In the mixed standard solution, the retention time of the Vitamin K1 isotope marker (D7-Vitamin K1) was 4.700 min, and the retention time of the Vitamin K2 isotope marker (D7-Vitamin K2) was 3.600 min.

Example 4

Treatment of the Serum Sample

10 µL, which was the same amount as in the mixed standard solutions, of the mixed internal standard working solution was pipetted, 20 µL of serum sample was added to the pipetted mixed internal standard working solution, then two extraction reagents, i.e., 100 µL of methanol and 1000 µL of n-hexane, were added, and the obtained mixture was mixed with vortexes and oscillation at 2500 r/min for 10 min and then centrifuged at a high speed of 14000 r/min for 10 min 900 µL of the supernatant obtained after the centrifugation was taken, blown to dry with nitrogen, redissolved with 100 µL of methanol, and then mixed with vortexes and oscillation at 2500 r/min for 1 min to obtain the analytical sample.

Example 5

Detection of Vitamin K1 and Vitamin K2 in Traces of Serum Sample Based on the Standard Curve Equations Given in Example 3 and the Supernatant Obtained in Example 4

The supernatant obtained in Example 4 was detected using the constructed two-dimensional liquid chromatography-tandem mass spectrometer to obtain spectra of the serum sample.

Chromatographic peak areas of Vitamin K1, Vitamin K2, Vitamin K1 isotope marker (D7-Vitamin K1) and Vitamin K2 isotope marker (D7-Vitamin K2) in the serum sample were obtained from the spectra of the serum sample.

The ratio of the chromatographic peak area of Vitamin K1 to the chromatographic peak area of the Vitamin K1 isotope marker (D7-Vitamin K1) in the serum sample was used as y1, and substituted into $y1=a*x1+b$ to obtain the ratio x1 of the concentration of Vitamin K1 to the concentration of the Vitamin K1 isotope marker (D7-Vitamin K1) in the serum sample. Since the concentration of the Vitamin K1 isotope marker (D7-Vitamin K1) was known, the concentration of Vitamin K1 in the serum sample could be calculated.

Similarly, the ratio of the chromatographic peak area of Vitamin K2 to the chromatographic peak area of the Vitamin K2 isotope marker (D7-Vitamin K2) in the serum sample was used as y2, and substituted into $y2=c*x2+d$ to obtain the ratio x2 of the concentration of Vitamin K2 to the concentration of the Vitamin K2 isotope marker (D7-Vitamin K2) in the serum sample. Since the concentration of the Vitamin K2 isotope marker (D7-Vitamin K2) was known, the concentration of Vitamin K2 in the serum sample could be calculated.

In this example, the chromatographic conditions for the high performance liquid chromatography of the liquid chromatography-tandem mass spectrometer and the spectrometry conditions for the spectrometry were the same as the chromatographic conditions and spectrometry conditions in Example 3, which will not be repeated herein.

Figure 5:
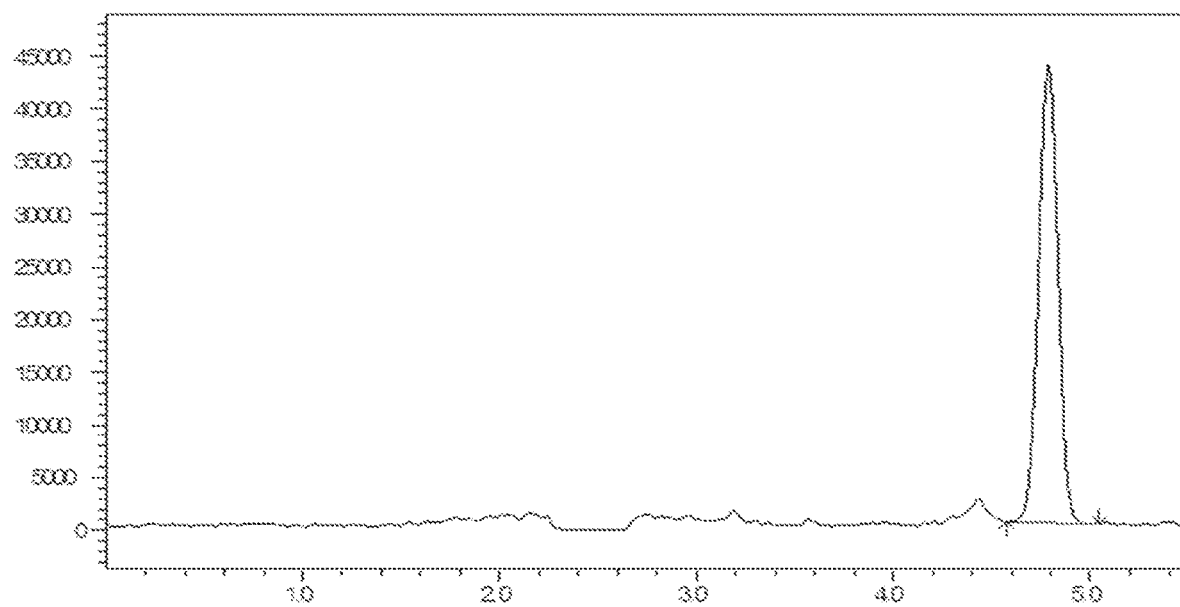
FIG. 5 is a chromatogram of Vitamin K1 in a blood sample provided by an example of the present disclosure.
Figure 6:
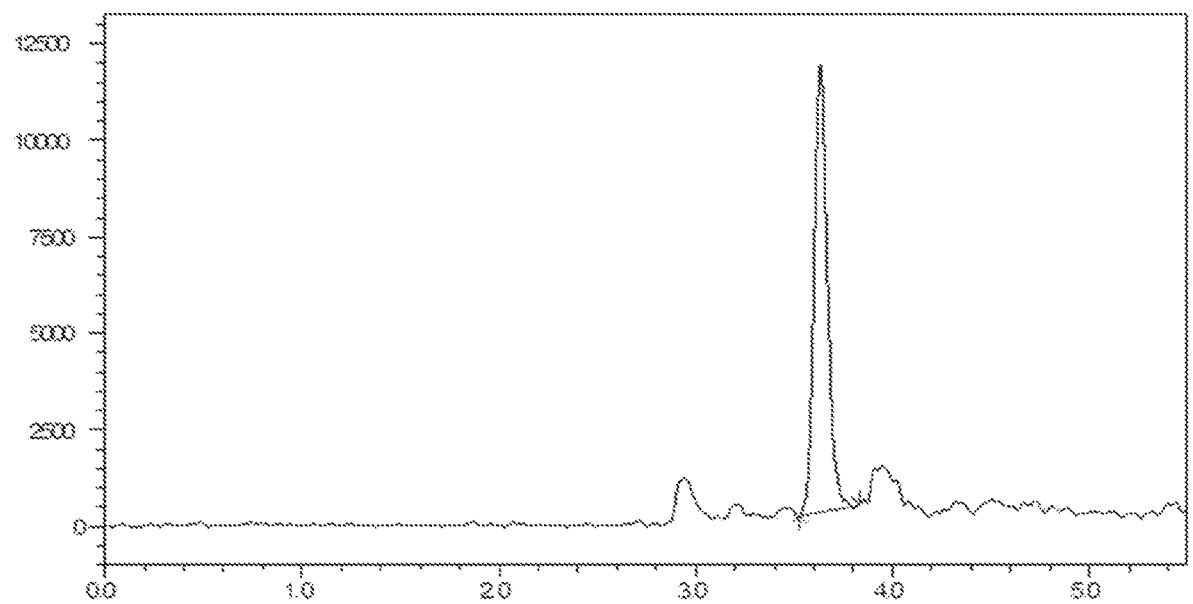
FIG. 6 is a chromatogram of Vitamin K2 in a blood sample provided by an example of the present disclosure.
Figure 7:
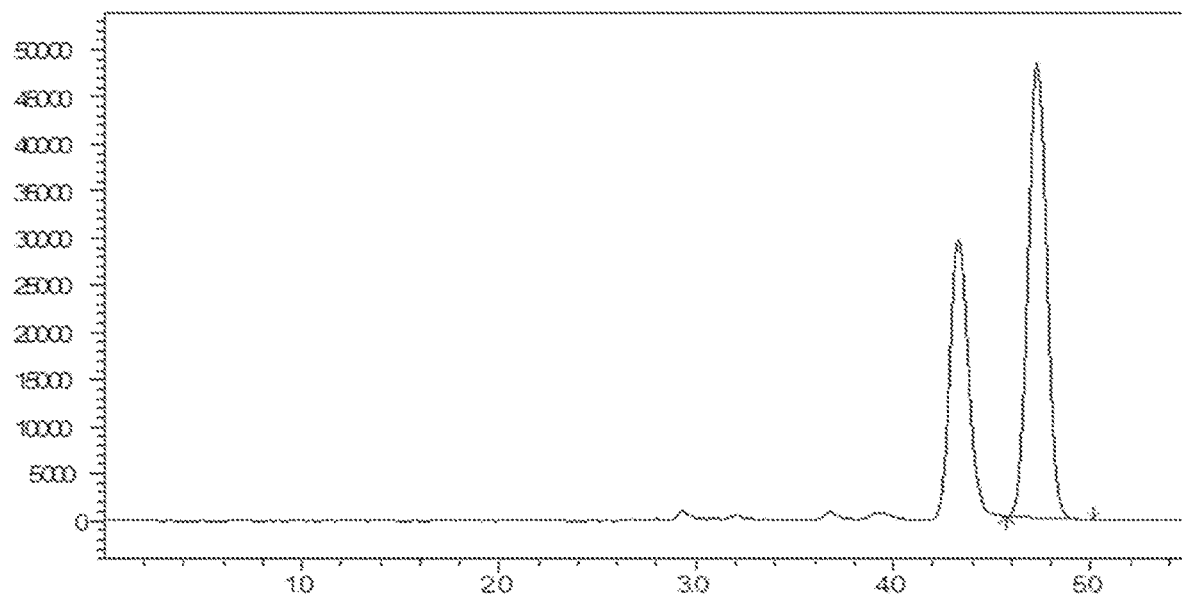
FIG. 7 is a chromatogram of a Vitamin K1 isotope marker (D7-Vitamin K1) in a blood sample provided by an example of the present disclosure.
Figure 8:
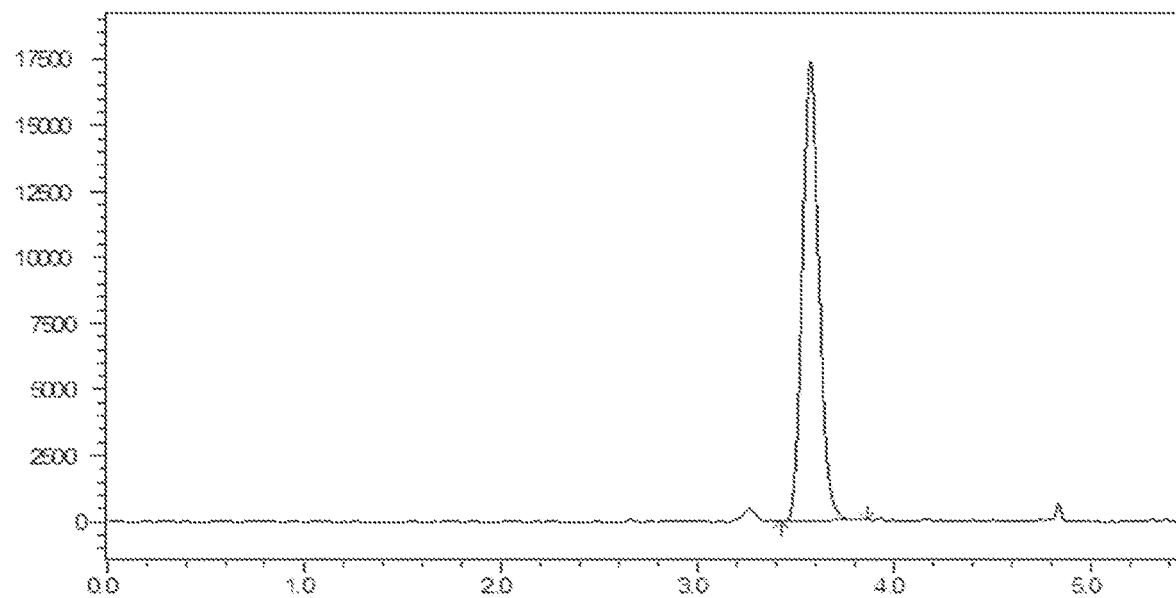
FIG. 8 is a chromatogram of a Vitamin K2 isotope marker (D7-Vitamin K2) in a blood sample provided by an example of the present disclosure.

The chromatogram of Vitamin K1 in the serum sample was shown in FIG. 5, the chromatogram of Vitamin K2 in the serum sample was shown in FIG. 6, the chromatogram of the Vitamin K1 isotope marker (D7-Vitamin K1) in the serum sample was shown in FIG. 7, and the chromatogram of the Vitamin K2 isotope marker (D7-Vitamin K2) in the serum sample was shown in FIG. 8.

In the serum sample, the retention time of Vitamin K1 was 4.700 min, and the retention time of Vitamin K2 was 3.600 min.

In the serum sample, the retention time of the Vitamin K1 isotope marker (D7-Vitamin K1) was 4.700 min, and the retention time of the Vitamin K2 isotope marker (D7-Vitamin K2) was 3.600 min.

It can be seen, from the comparison of the retention time of Vitamin K1 and Vitamin K2 in the mixed standard solutions and the retention time of Vitamin K1 and Vitamin K2 in the serum sample, that the retention time of the target substances in the mixed standard solutions was consistent with the retention time of the corresponding target substances in the serum sample. Moreover, by using the Vitamin K1 isotope marker (D7-Vitamin K1) and the Vitamin K2 isotope marker (D7-Vitamin K2) as the internal standard substances, the identification of Vitamin K1 and Vitamin K2 was more accurate with short analysis time and small interference, and the internal standard quantitation had strong specificity, high accuracy and high sensitivity.

It is to be noted that in FIGS. 1 to 8, the abscissa is the collection time, and the ordinate is the ion signal strength.

Example 6

Linear Relation and Quantification Limit of the Method for Detecting Vitamin K1 and Vitamin K2 in the Serum Sample Steps of Example 3 were performed on each of 9 mixed standard solutions of different concentrations prepared in Example 2 to obtain chromatograms. Diagrams were plotted based on chromatographic peak area-concentration to obtain standard curves. The results showed that the linear ranges of Vitamin K1 and Vitamin K2 were as follows:

(1) Linear Range

Vitamin K1 has good linearity in the range of 0.05 ng/mL to 500.00 ng/mL with a correlation coefficient of $R^2>0.99$.

Vitamin K2 has good linearity in the range of 0.05 ng/mL to 500.00 ng/mL with a correlation coefficient of $R^2>0.99$.

Samples with low levels of Vitamin K1 and Vitamin K2 were selected from serum samples of volunteers. These selected samples were diluted with saline as the solvent to obtain a series of diluted serum samples in different dilution proportions. The diluted serum samples were pre-treated according to Example 4, and the sample injection was performed according to Example 5 to obtain detection results and chromatograms. The limit of detection (LOD) was obtained with the target substance signal-to-noise ratio as 3, and the limit of quantification (LOQ) was obtained with the target substance signal-to-noise ratio as 10. The results showed that the LOD and the LOQ of Vitamin K1 and Vitamin K2 were as follows:

(2) Limit of Detection (LOD)
Vitamin K1:0.011 ng/mL
Vitamin K2:0.037 ng/mL
(3) Limit of Quantification (LOQ)
Vitamin K1:0.013 ng/mL
Vitamin K2:0.043 ng/mL Example 7

Recovery and Precision of the Method for Detecting Vitamin K1 and Vitamin K2 in Traces of Serum Sample Any three mixed standard solutions in Example 2 were taken and then prepared into solutions of three different concentrations: high, medium, and low for the recovery experiment and precision experiment. The prepared solutions were detected according to the treatment manner and detection conditions in Examples 2 to 5, and the analysis and measurements were repeated for 3 batches to obtain the recovery and precision of Vitamin K1 and Vitamin K2 in the serum sample. The results are shown in Table 2.

TABLE 2

| Detection index | Theoretical spiking concentration (ng/mL) | Average recovery % | Precision % |
|---|---|---|---|
| Vitamin K1 | 0.20 | 103.2 | 5.58 |
|  | 2.00 | 106.7 | 3.26 |
|  | 200.00 | 94.0 | 1.03 |
| Vitamin K2 | 0.20 | 107.7 | 5.18 |
|  | 2.00 | 103.2 | 4.38 |
|  | 200.00 | 91.5 | 1.12 |

From the above validation tests, the average recovery, limit of detection, precision and other technical indexes of this example met the requirements. It can be seen that the method for simultaneously detecting Vitamin K1 and Vitamin K2 in traces of blood of the present application had high sensitivity, strong specificity, great reproducibility, and high accuracy.

Example 8

Detection of Vitamin K1 and Vitamin K2 in Serum Using a One-Dimensional Liquid Chromatography-Tandem Mass Spectrometer The content in Examples 1 to 5 was repeated herein, only except that the two-dimensional liquid chromatography was replaced by the one-dimensional liquid chromatography in which the chromatographic column was Kinetex Phenyl-Hexyl 2.6 μm 100*4.6 mm while other pre-treatment conditions and detection conditions remained unchanged. Vitamin K1 and Vitamin K2 in traces of serum sample were detected.

Figure 9:
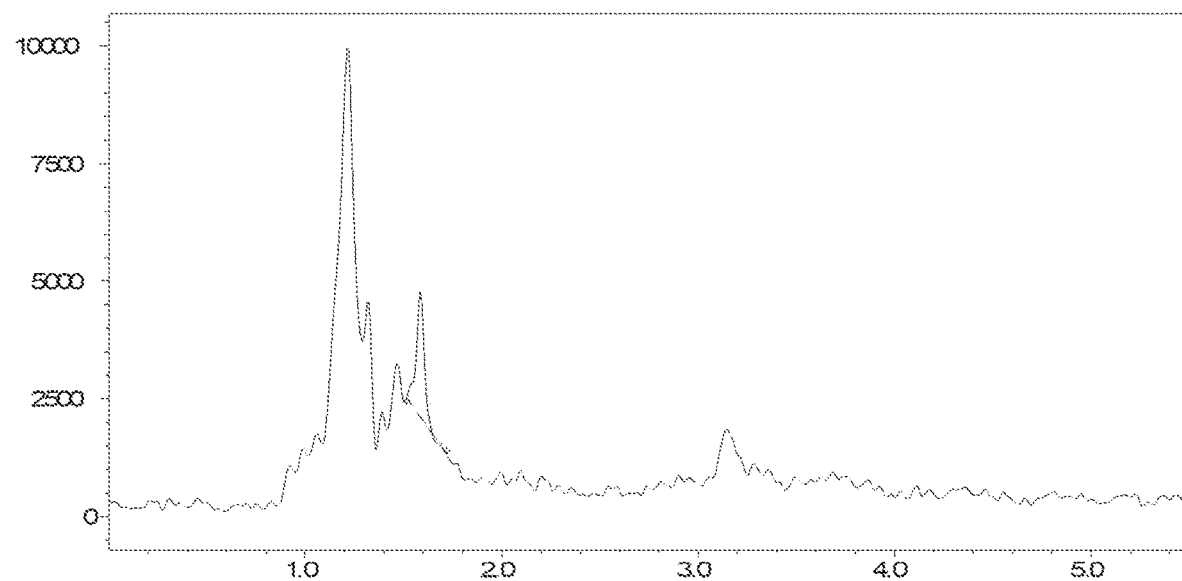
FIG. 9 is a chromatogram of Vitamin K1 in a blood sample provided by an example of the present disclosure.
Figure 10:
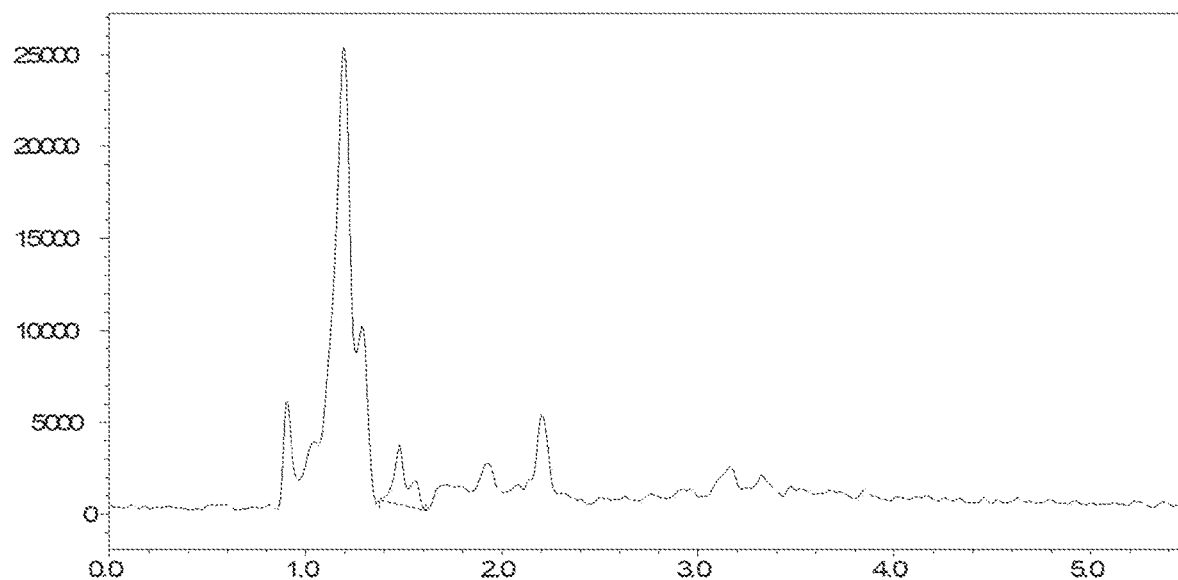
FIG. 10 is a chromatogram of Vitamin K2 in a blood sample provided by an example of the present disclosure.

The chromatogram of Vitamin K1 in the serum sample was shown in FIG. 9, and the chromatogram of Vitamin K2 in the serum sample was shown in FIG. 10. It can be known from the figures that there was no smooth baseline and good separation.

Example 9

Detection of Vitamin K1 and Vitamin K2 in Serum Using a One-Dimensional Liquid Chromatography-Tandem Mass Spectrometer The content in Examples 1 to 5 was repeated herein, only except that the two-dimensional liquid chromatography was replaced by the one-dimensional liquid chromatography in which the chromatographic column was Kinetex C18 2.6 μm 100*4.6 mm while other pre-treatment conditions and detection conditions remained unchanged. Vitamin K1 and Vitamin K2 in traces of serum sample were detected.

Figure 11:
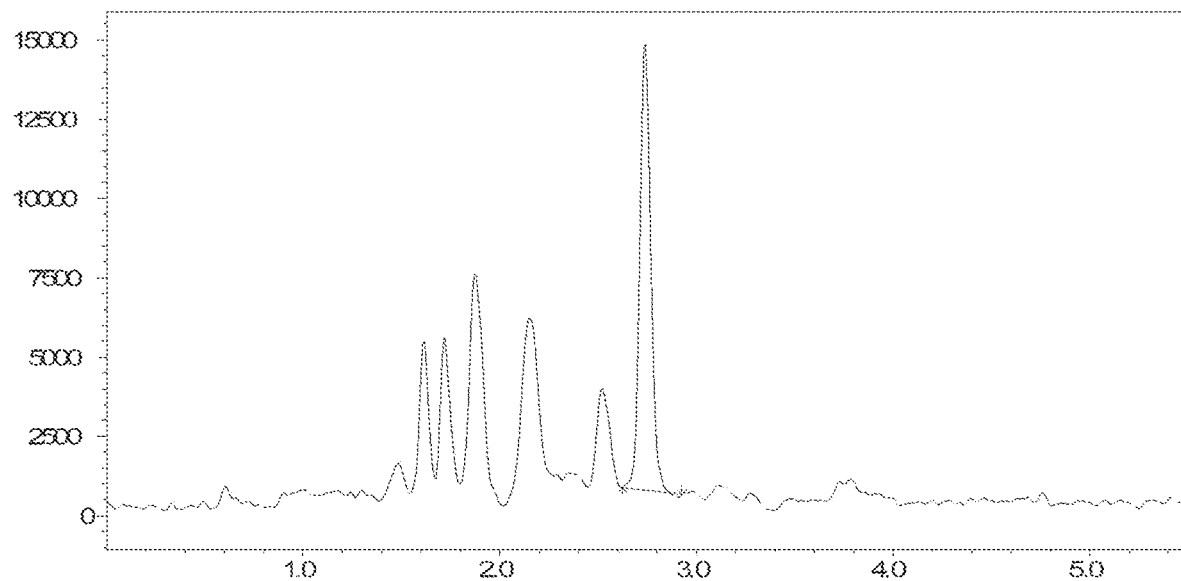
FIG. 11 is a chromatogram of Vitamin K1 in a blood sample provided by an example of the present disclosure.
Figure 12:
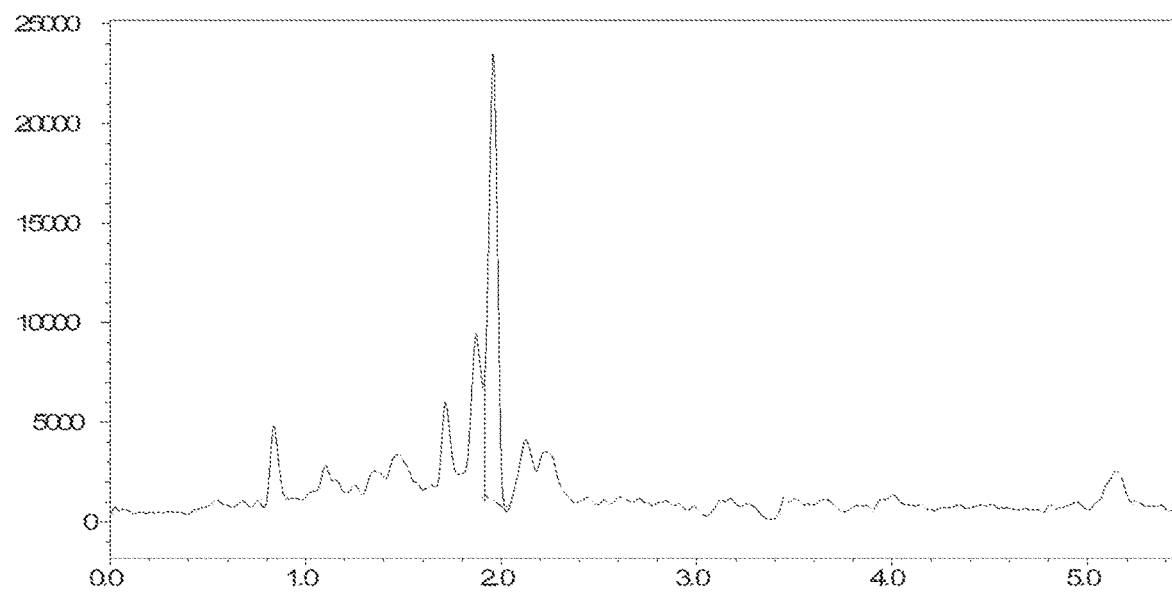
FIG. 12 is a chromatogram of Vitamin K2 in a blood sample provided by an example of the present disclosure.

The chromatogram of Vitamin K1 in the serum sample was shown in FIG. 11, and the chromatogram of Vitamin K2 in the serum sample was shown in FIG. 12. It can be known from the figures that there was no smooth baseline and good separation.

Example 10

Detection of Vitamin K1 and Vitamin K2 in Serum Using a One-Dimensional Liquid Chromatography-Tandem Mass Spectrometer The content in Examples 1 to 5 was repeated herein, and the only except that the two-dimensional liquid chromatography was replaced by the one-dimensional liquid chromatography in which the chromatographic column was Kinetex F5 2.6 μm 100*4.6 mm while other pre-treatment conditions and detection conditions remained unchanged. Vitamin K1 and Vitamin K2 in traces of serum sample were detected.

Figure 13:
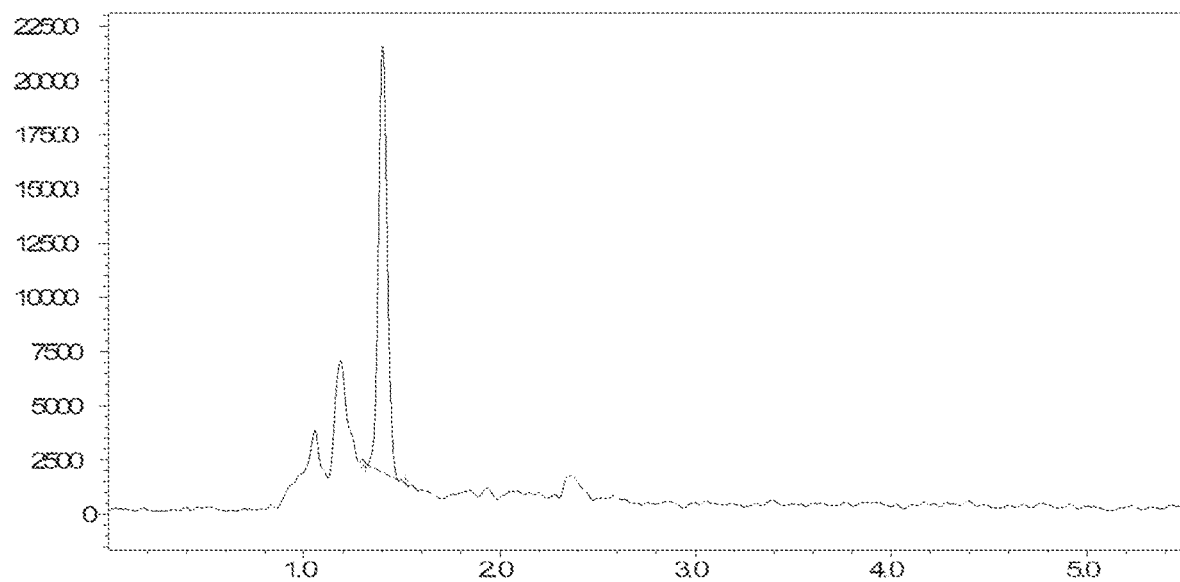
FIG. 13 is a chromatogram of Vitamin K1 in a blood sample provided by an example of the present disclosure.
Figure 14:
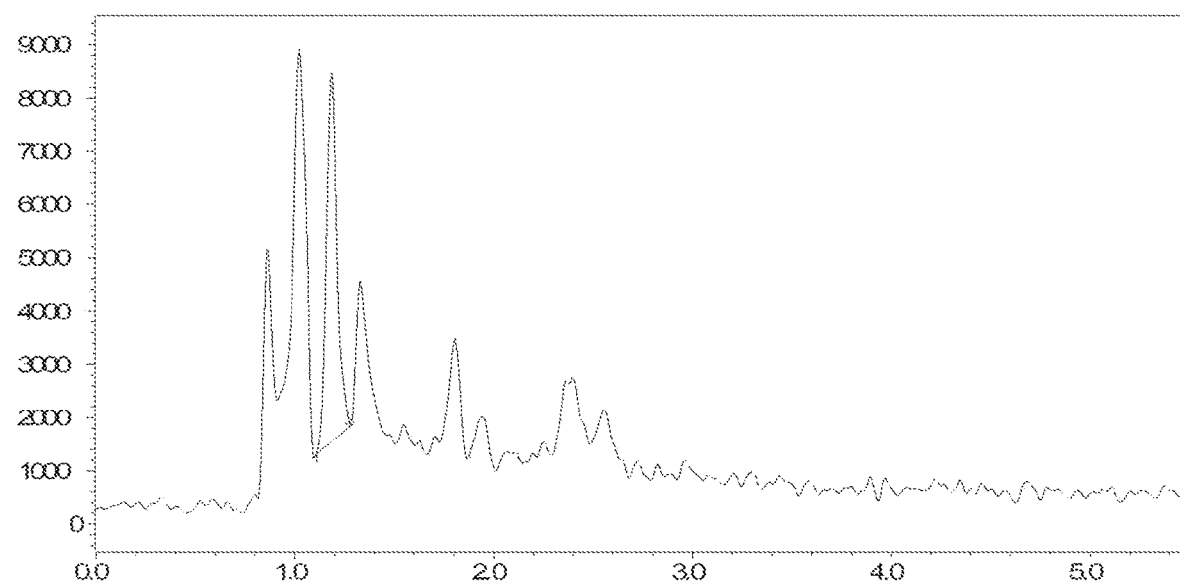
FIG. 14 is a chromatogram of Vitamin K2 in a blood sample provided by an example of the present disclosure.

The chromatogram of Vitamin K1 in the serum sample was shown in FIG. 13, and the chromatogram of Vitamin K2 in the serum sample was shown in FIG. 14. It can be known from the figures that there was no smooth baseline and good separation.

In conclusion, the retention capacity was as follows: Example 9>Example 8>Example 10. However, for the detection of VK1 and VK2 in the serum sample using the one-dimensional liquid chromatography with the above three chromatographic columns, the smooth baseline and good separation could not be obtained.

Example 11

Discussion of the Selection of the One-Dimensional Chromatographic Column and the Two-Dimensional Chromatographic Column in the Two-Dimensional Liquid Chromatography-Tandem Mass Spectrometer (1) The content in Examples 1 to 5 was repeated herein, only except that the first dimensional chromatographic column was Kinetex Phenyl-Hexyl 2.6 μm 100*4.6 mm, and the second dimensional chromatographic column was Kinetex C18 2.6 μm 100*4.6 mm. Other pre-treatment conditions and detection conditions remained unchanged. Vitamin K1 and Vitamin K2 in traces of serum sample were detected.

Figure 15:
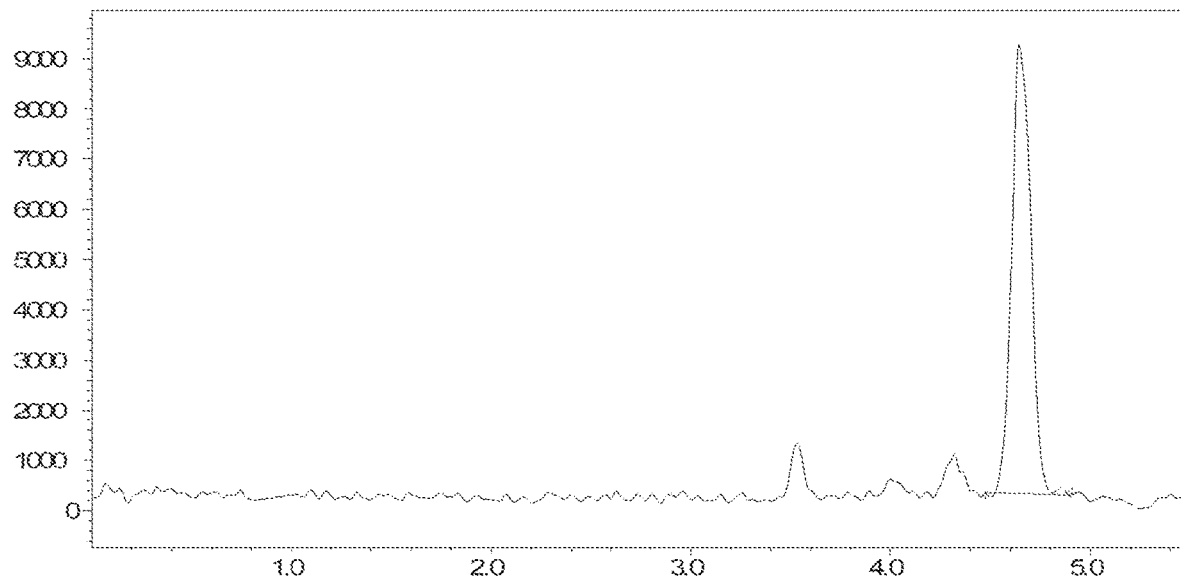
FIG. 15 is a chromatogram of Vitamin K1 in a blood sample provided by an example of the present disclosure.
Figure 16:
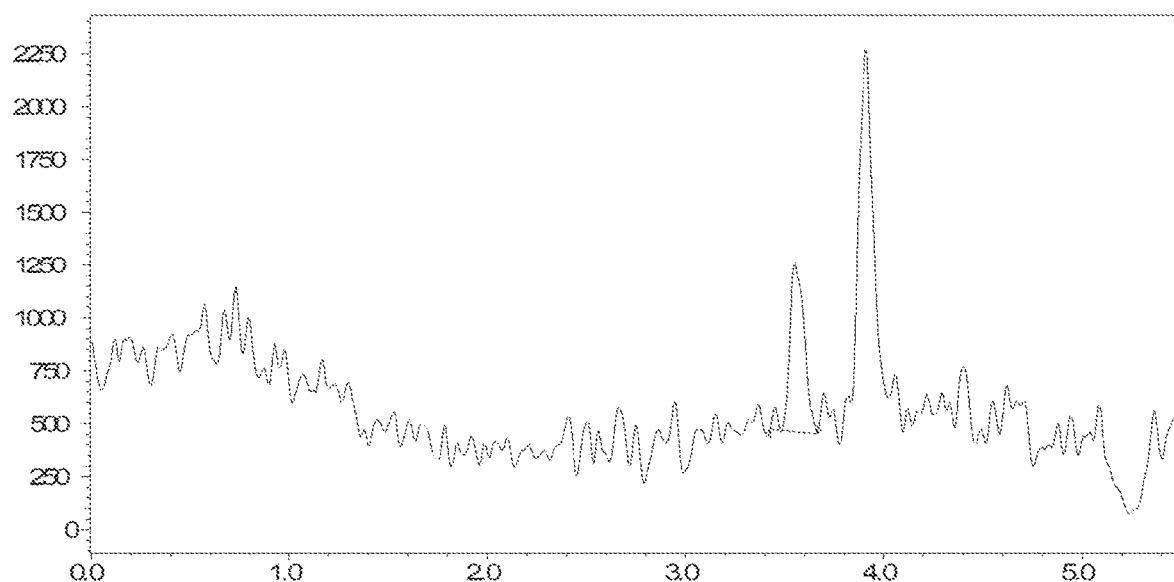
FIG. 16 is a chromatogram of Vitamin K2 in a blood sample provided by an example of the present disclosure.

The chromatogram of Vitamin K1 in the serum sample was shown in FIG. 15, and the chromatogram of Vitamin K2 in the serum sample was shown in FIG. 16. It can be known from the figures that the smooth baseline and good separation could be obtained through such a chromatographic column combination.

(2) The only difference between (2) and (1) was that in (2), the sequence of these two types of chromatographic columns was changed, that is, the first dimensional chromatographic column was Kinetex C18 2.6 μm 100*4 6 mm, and the second dimensional chromatographic column was Kinetex Phenyl-Hexyl 2.6 μm 100*4.6 mm. Other pre-treatment conditions and detection conditions remained unchanged. Vitamin K1 and Vitamin K2 in traces of serum sample were detected.

Figure 17:
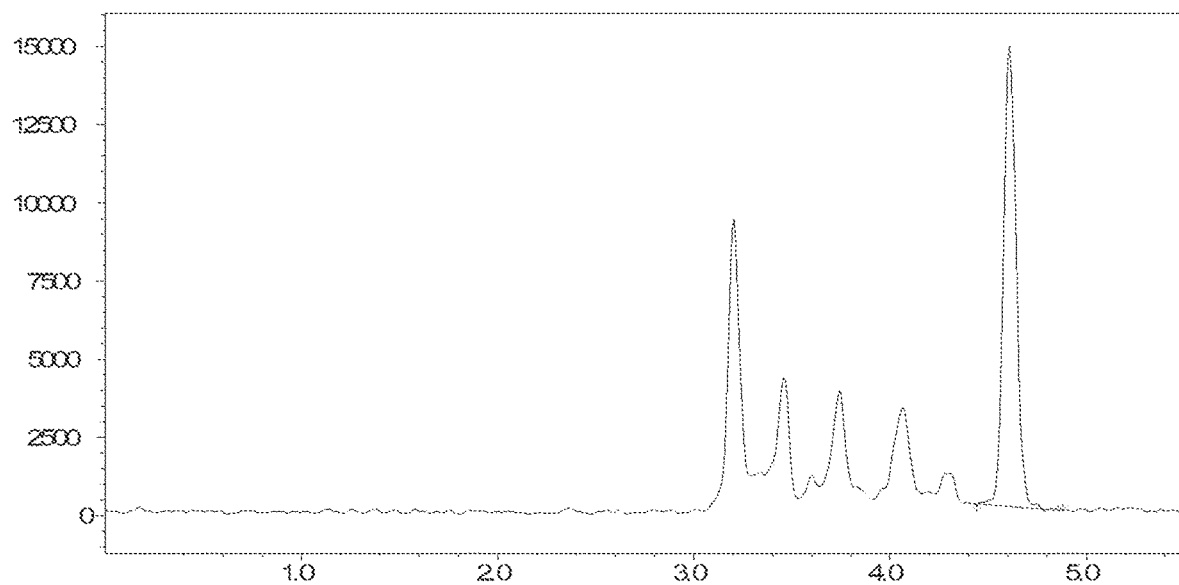
FIG. 17 is a chromatogram of Vitamin K1 in a blood sample provided by an example of the present disclosure.
Figure 18:
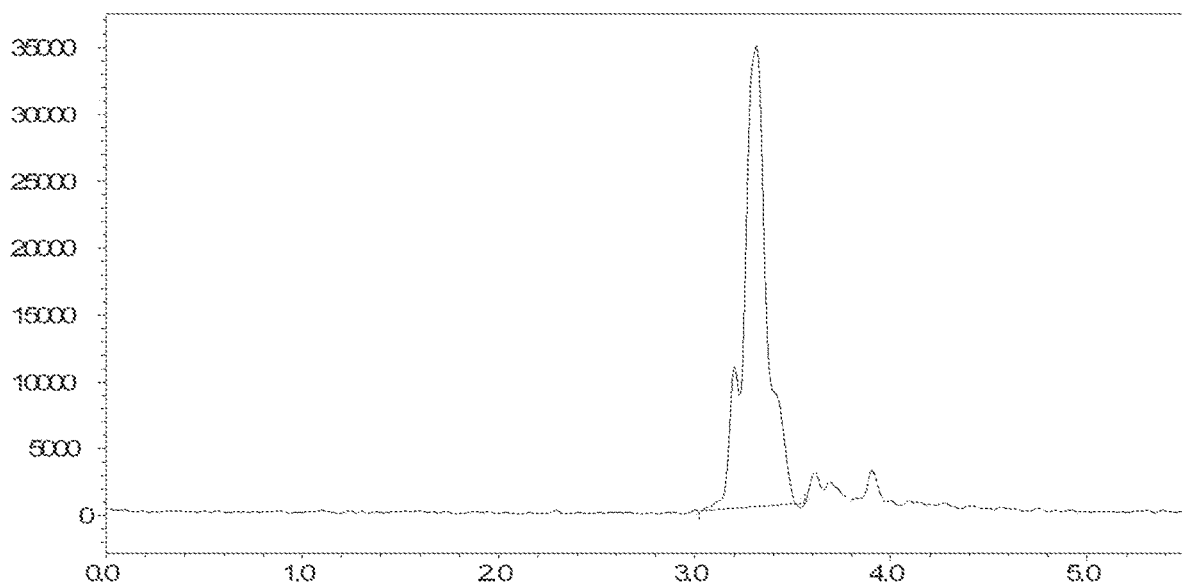
FIG. 18 is a chromatogram of Vitamin K2 in a blood sample provided by an example of the present disclosure.

The chromatogram of Vitamin K1 in the serum sample was shown in FIG. 17, and the chromatogram of Vitamin K2 in the serum sample was shown in FIG. 18. It can be known from the figures that with such a chromatographic column combination, impurities in front of the target peak increased, resulting in an elevated baseline in front of the chromatographic peak and thus affecting the detection.

In conclusion, the sequence of chromatographic columns in the detection method in the present application had a key role in the detection.

(3) The content in Examples 1 to 5 was repeated herein, only except that the first dimensional chromatographic column was Kinetex F5 2.6 μm 100*4 6 mm, and the second dimensional chromatographic column was Kinetex C18 2.6 μm 100*4.6 mm. Other pre-treatment conditions and detection conditions remained unchanged. Vitamin K1 and Vitamin K2 in traces of serum sample were detected.

Figure 19:
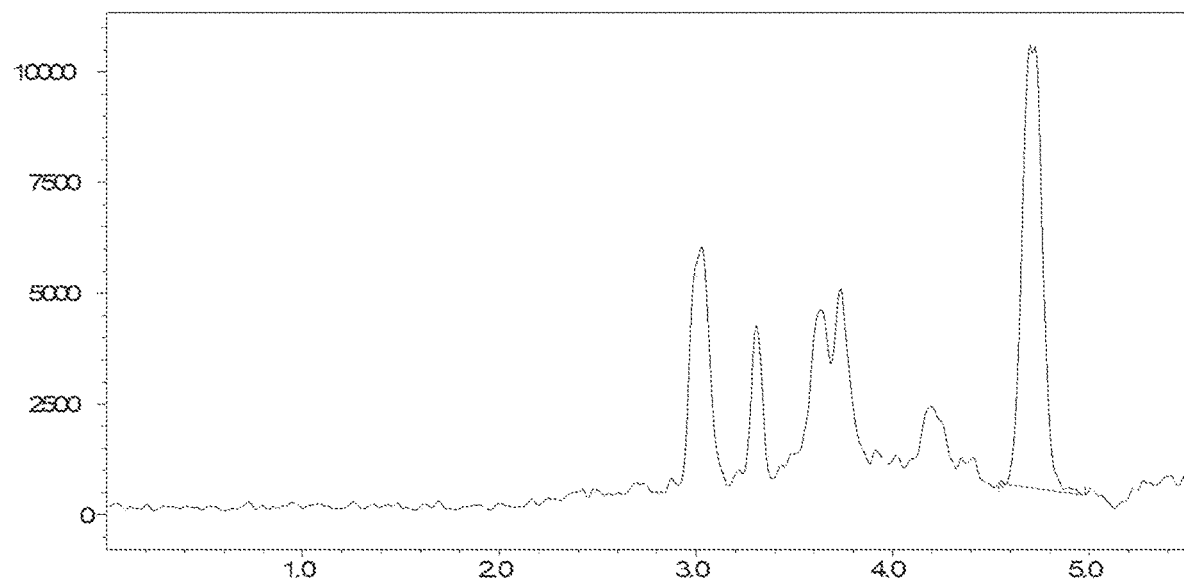
FIG. 19 is a chromatogram of Vitamin K1 in a blood sample provided by an example of the present disclosure.
Figure 20:
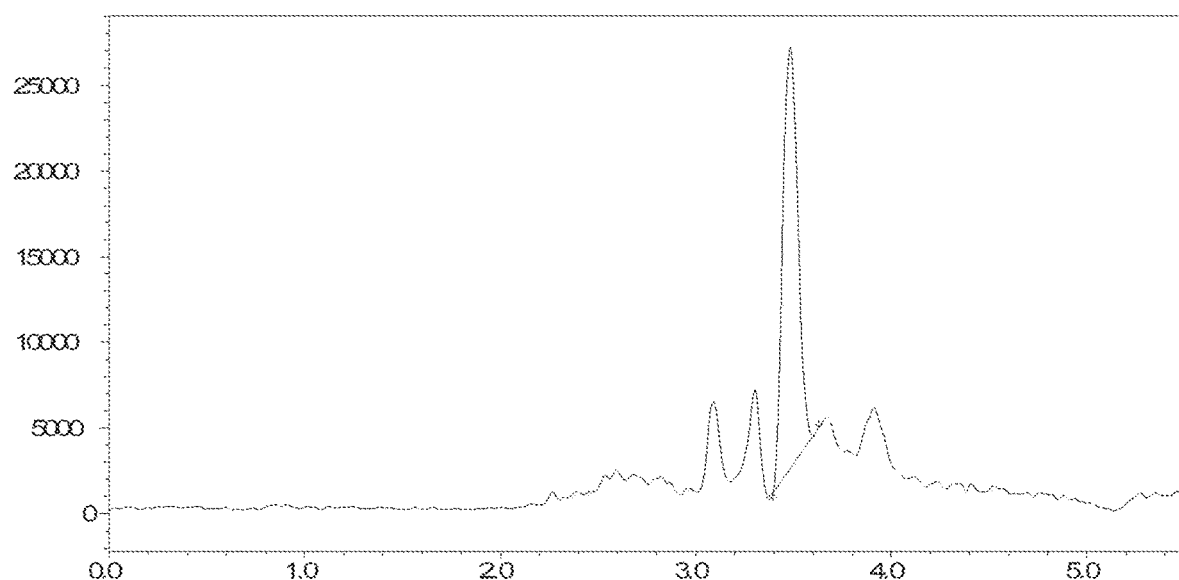
FIG. 20 is a chromatogram of Vitamin K2 in a blood sample provided by an example of the present disclosure.

The chromatogram of Vitamin K1 in the serum sample was shown in FIG. 19, and the chromatogram of Vitamin K2 in the serum sample was shown in FIG. 20. It can be known from the figures that such a chromatographic column combination failed to provide the smooth baseline and good impurity separation.

(4) The content in Examples 1 to 5 was repeated herein, only except that the first dimensional chromatographic column was Kinetex Phenyl-Hexyl 2.6 μm 100*4.6 mm, and the second dimensional chromatographic column was Kinetex F5 2.6 μm 100*4.6 mm. Other pre-treatment conditions and detection conditions remained unchanged. Vitamin K1 and Vitamin K2 in traces of serum sample were detected.

Figure 21:
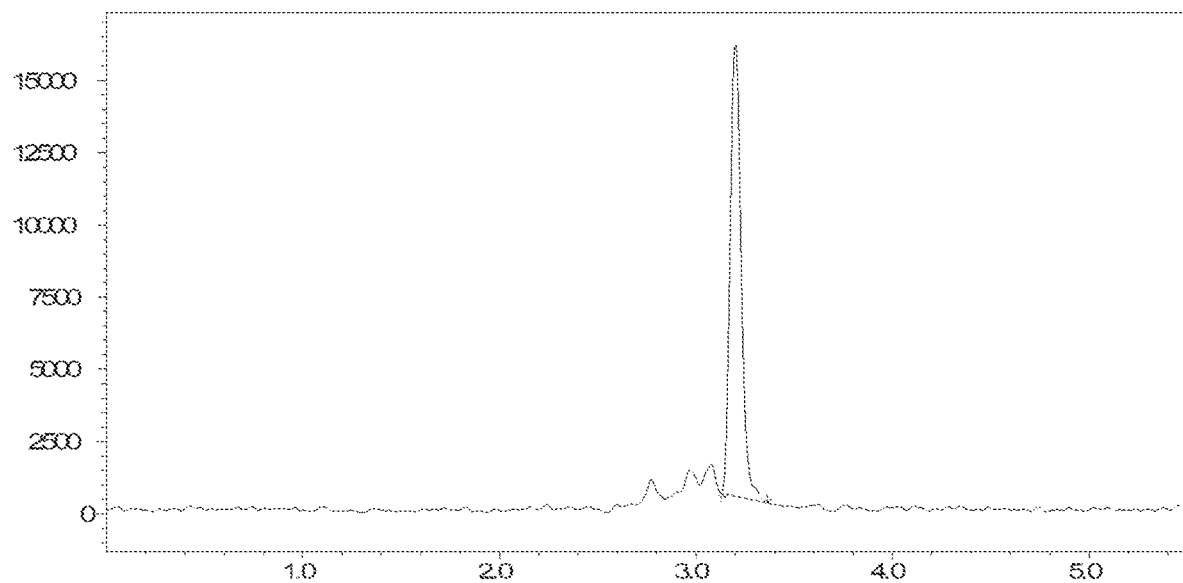
FIG. 21 is a chromatogram of Vitamin K1 in a blood sample provided by an example of the present disclosure.
Figure 22:
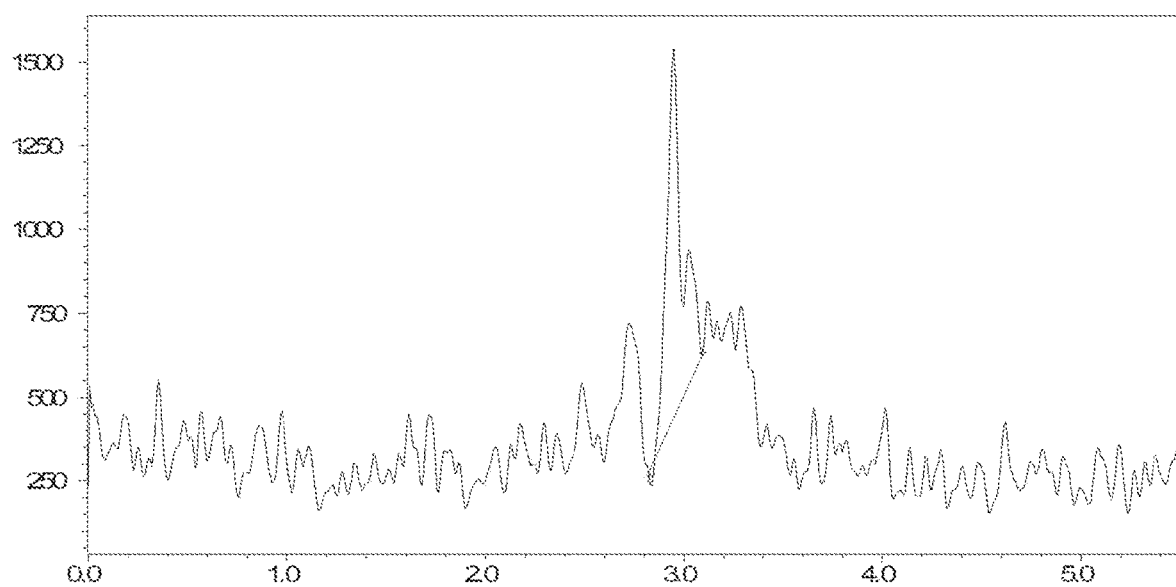
FIG. 22 is a chromatogram of Vitamin K2 in a blood sample provided by an example of the present disclosure.

The chromatogram of Vitamin K1 in the serum sample was shown in FIG. 21, and the chromatogram of Vitamin K2 in the serum sample was shown in FIG. 22. It can be known from the figures that such a chromatographic column combination failed to provide the smooth baseline and good impurity separation.

In conclusion, only when the phenylhexyl column is specifically selected as the first dimensional chromatographic column and the C18 column as the second dimensional chromatographic column can the best separation of endogenous impurities in blood be implemented.

It can be known from detection results of the above examples the following points.

(1) The present application constructs a two-dimensional liquid chromatography-tandem mass spectrometer, and implements the simultaneous detection of Vitamin K1 and Vitamin K2 in blood using the two-dimensional liquid chromatography-tandem mass spectrometer, especially the detection of traces of blood sample, where the blood sample includes serum, plasma and whole blood, and the usage amount of the sample is 20-200 μL.

(2) In the present application, the detection of Vitamin K1 and Vitamin K2 provides a pair of quantitative ions and qualitative ions, and at the same time, the isotope markers of Vitamin K1 and Vitamin K2 are used as the internal standard substance, thereby making the identification and quantification of Vitamin K1 and Vitamin K2 in the blood sample more accurate.

(3) In the present application, the pre-treatment of the blood sample only includes simple steps of adding samples, taking samples, mixing, centrifuging, nitrogen blowing and re-dissolving, and thus can be easily automated in production, thereby greatly reducing the pre-treatment time in the analysis of batches of samples and improving the detection efficiency.

(4) In the present application, the detection of Vitamin K1 and Vitamin K2 of a single sample can be completed within 5.5 min, and the analysis is performed through the constructed two-dimensional liquid chromatography-tandem mass spectrometer, implementing the fast analysis and high sensitivity.

It is to be noted that as used herein, relationship terms such as "first" and "second" are used merely to distinguish one entity or operation from another. It does not necessarily require or imply any such actual relationship or order between these entities or operations. Furthermore, the term "comprising", "including" or any other variant thereof is intended to encompass a non-exclusive inclusion so that a process, method, article or device that includes a series of elements not only includes the expressly listed elements but may also include other elements that are not expressly listed or are inherent to such process, method, article or device. In the absence of more restrictions, the elements defined by the statement "including a . . . " do not exclude the presence of additional identical elements in the process, method, article or device that includes the elements.

Finally, it is to be noted that the above are only preferred examples of the present disclosure, which are only used to illustrate the technical solutions of the present invention, and are not intended to limit the scope of the present disclosure. Therefore, the scope of protection of the present disclosure is defined by the appended claims.

What is claimed is:

1. A method for simultaneously detecting Vitamin K1 and Vitamin K2 in blood, comprising:
    (1) establishment of an analytical method for detecting Vitamin K1 and Vitamin K2 in blood, comprising selection of two-dimensional liquid chromatography-tandem mass spectrometer system modules, construction of a two-dimensional liquid chromatography-tandem mass spectrometer system, and establishment of analytical conditions of the two-dimensional liquid chromatography-tandem mass spectrometer,
    (2) standardization of standard solutions
    (2a) preparing at least three mixed standard solutions, wherein the mixed standard solution is a solution having an internal standard substance, Vitamin K1, and Vitamin K2, and the concentration of the internal standard substance in the at least three mixed standard solutions is the same;
    (2b) detecting each of the at least three mixed standard solutions with the two-dimensional liquid chromatography-tandem mass spectrometer using the analytical method established in Step (1) to obtain first detection results respectively corresponding to the at least three mixed standard solutions; and
    (2c) fitting standard curve equations respectively corresponding to Vitamin K1 and Vitamin K2 according to each of the first detection results and concentrations of the internal standard substance, Vitamin K1 and Vitamin K2 in the mixed standard solutions; and
    (3) detection of a blood sample
    (3a) adding the same amount of internal standard substance as in the mixed standard solution to the blood sample, adding an extraction reagent, performing centrifugation after the extraction, collecting a supernatant obtained after the centrifugation, blowing the supernatant to dry, and redissolving the residue with a redissolution solution to obtain an analytical sample;

(3b) detecting the blood sample with the two-dimensional liquid chromatography-tandem mass spectrometer using the analytical method established in Step (1) to obtain a second detection result corresponding to the blood sample; and (3c) obtaining concentrations of Vitamin K1 and Vitamin K2 in the blood sample based on the second detection result and the standard curve equations respectively corresponding to Vitamin K1 and Vitamin K2;

wherein the establishment of the analytical conditions of the two-dimensional liquid chromatography-tandem mass spectrometer in Step (1) comprises:

selecting phenylhexyl as the first dimensional chromatographic column of two-dimensional liquid chromatography; and C18 as the second dimensional chromatographic column.

2. The method according to claim 1, wherein the two-dimensional liquid chromatography-tandem mass spectrometer system modules in Step (1) comprise a liquid chromatography pump, an auto sampler, a column oven, and a mass spectrum analyzer;

wherein the number of sets of liquid chromatography pumps is at least two, wherein one of the at least two sets of liquid chromatography pumps is connected to the auto sampler, and the resting of the at least two sets of liquid chromatography pumps complete a liquid-pumping process independently;

the auto sampler is used for completing a sample injection process; and the column oven comprises at least one set of switching valves and is used for completing a two-dimensional liquid chromatography column switching process; and each of the at least one set of switching valves is independently selected from a six-way switching valve or a ten-way switching valve.

3. The method according to claim 1, wherein the construction of the two-dimensional liquid chromatography-tandem mass spectrometer system in Step (1) comprises:

connecting one set of liquid chromatography pumps in series to the auto sampler, connecting the auto sampler to a first dimensional chromatographic column, and connecting the first dimensional chromatographic column to the switching valve; connecting another set of liquid chromatography pumps to the switching valve, connecting the switching valve to a second dimensional chromatographic column, and connecting the second dimensional chromatographic column to the mass spectrum analyzer; and controlling an analysis state of the system through the switching valve, wherein the analysis state comprises three states i.e. sample injection, two-dimensional transfer, and analysis;

when the analysis state of the system is the sample injection state, a sample is analyzed by the first dimensional chromatographic column, and non-target analytes are discharged as a waste liquid from the switching valve;

when the analysis state of the system is the two-dimensional transfer state, the first dimensional chromatographic column is connected in series to the second dimensional chromatographic column, and a target analyte is transferred from the first dimensional chromatographic column to the second dimensional chromatographic column; and when the analysis state of the system is the analysis state, the sample is analyzed by the second dimensional chromatographic column, and the mass spectrum analyzer is connected to perform data collection.

4. The method according to claim 1, wherein the establishment of the analytical conditions of the two-dimensional liquid chromatography-tandem mass spectrometer in Step (1) comprises:

setting a flow rate of a mobile phase of two-dimensional liquid chromatography to 0.5-2.0 mL/min;

wherein the mobile phase is a polar solvent comprising ultrapure water, methanol, acetonitrile, and any mixture of any two or three thereof in any ratio; and the mobile phase comprises 0.01% to 1% formic acid;

setting a sample injection amount of two-dimensional liquid chromatography to 1-100 μL;

setting a column temperature of the column oven of two-dimensional liquid chromatography to 20-60° C.;

configuring the mass spectrum analyzer to adopt an atmospheric pressure chemical ionization (APCI) source and a positive ion scan mode; and setting a flow rate of atomized gas to 0.5-3 L/min, a flow rate of heated gas to 3-20 L/min, a temperature of an ion source to 100-400° C., a temperature of a desolvent tube to 30-300° C., a temperature of a heating block to 30-500° C., a flow rate of dry gas to 0-20 L/min, and an interface voltage to 1-5 kV.

5. The method according to claim 1, wherein the internal standard substance comprises a Vitamin K1 isotope marker and a Vitamin K2 isotope marker.

6. The method according to claim 1, wherein two variables of the standard curve equation corresponding to Vitamin K1 are: a ratio of a chromatographic peak area of Vitamin K1 to a chromatographic peak area of an internal standard substance corresponding to Vitamin K1, and a ratio of a concentration of Vitamin K1 to a concentration of the internal standard substance corresponding to Vitamin K1, respectively; and two variables of the standard curve equation corresponding to Vitamin K2 are: a ratio of a chromatographic peak area of Vitamin K2 to a chromatographic peak area of an internal standard substance corresponding to Vitamin K2, and a ratio of a concentration of Vitamin K2 to a concentration of the internal standard substance corresponding to Vitamin K2, respectively.

7. The method according to claim 1, wherein a method for preparing the at least three mixed standard solutions in Step (2a) comprises:

preparing standard mixed intermediate solutions: mixing a Vitamin K1 standard stock solution and a Vitamin K2 standard stock solution in different proportions, diluting the obtained mixed solutions with a diluent to obtain the standard mixed intermediate solutions of at least three different concentrations, and storing the standard mixed intermediate solutions from light;

preparing a mixed internal standard working solution: mixing a Vitamin K1 internal standard substance stock solution and a Vitamin K2 internal standard substance stock solution in different proportions, diluting the obtained mixed solution with a diluent to obtain the mixed internal standard working solution, and storing the mixed internal standard working solution from light; and preparing the mixed standard solutions: pipetting the same volume of at least three standard mixed intermediate solutions that have different concentrations respectively, adding the same volume of the mixed internal standard working solution and the same volume of the diluent to each of the at least three standard mixed intermediate solutions, and mixing the obtained mixtures with vortexes at 1500-3000 r/min for 30 s to 1 min to prepare at least three different mixed standard solutions;

wherein the diluent comprises methanol or an aqueous methanol solution, acetonitrile or an aqueous acetonitrile solution, and isopropanol or an aqueous isopropanol solution, wherein volume concentrations of the aqueous methanol solution, the acetonitrile aqueous solution and the isopropanol aqueous solution are independently selected from 50% to 100%.

8. The method according to claim 7, wherein in the standard mixed intermediate solution, Vitamin K1 has a concentration of 0.05-500 ng/mL, and Vitamin K2 has a concentration of 0.05-500 ng/mL; and in the mixed internal standard working solution, the Vitamin K1 internal standard substance has a concentration of 10-30 ng/mL, and the Vitamin K2 internal standard substance has a concentration of 10-30 ng/mL.

9. The method according to claim 1, wherein the blood sample comprises whole blood, serum, or plasma.

10. The method according to claim 1, wherein the blood sample is used in an amount of 20 µL or more.

11. The method according to claim 1, wherein before Step 3(a), the method further comprises:

centrifuging the blood sample at a centrifugation speed of 1000-3000 r/min for 10-20 min, using a supernatant obtained after the centrifugation as the blood sample, and storing the blood sample at −80° C.

12. The method according to claim 1, wherein Step 3(a) comprises:

adding the same amount of internal standard substance as in the mixed standard solution to the blood sample, adding an extraction reagent, mixing the blood sample with vortexes and oscillation for 5-15 min at a rotating speed of 1000-2500 r/min after the extraction, centrifuging the blood sample for 5-15 min at a rotating speed of 10000-15000 r/min, collecting some or all of a supernatant obtained after the centrifugation, blowing the same to dry with nitrogen under a nitrogen blower, redissolving the residue with a redissolution solution, and mixing the obtained mixture with vortexes and oscillation at a rotating speed of 1000-2500 r/min for 1-5 min to obtain an analytical sample.

13. The method according to claim 1, wherein the extraction reagent is a combination of a polar extraction reagent and a non-polar extraction reagent;

the polar extraction reagent comprises any one or a combination of at least two of methanol, ethanol, acetonitrile, acetone, or isopropanol;

the non-polar extraction reagent comprises any one or a combination of at least two of n-hexane, cyclohexane, n-octane, or petroleum ether; and wherein the redissolution solution comprises any one or a combination of at least two of methanol, ethanol, or acetonitrile.

* * * * *